(12) United States Patent
Carlton-Foss

(10) Patent No.: US 8,217,795 B2
(45) Date of Patent: Jul. 10, 2012

(54) METHOD AND SYSTEM FOR FALL DETECTION

(76) Inventor: John Carlton-Foss, Weston, MA (US)

( * ) Notice: Subject to any disclaimer, the term of this patent is extended or adjusted under 35 U.S.C. 154(b) by 495 days.

(21) Appl. No.: 11/999,277

(22) Filed: Dec. 5, 2007

(65) Prior Publication Data
US 2008/0129518 A1 Jun. 5, 2008

Related U.S. Application Data

(60) Provisional application No. 60/873,108, filed on Dec. 5, 2006.

(51) Int. Cl.
G08B 23/00 (2006.01)
(52) U.S. Cl. ............ 340/573.1; 340/825.19; 340/539.12
(58) Field of Classification Search ............... 340/573.1, 340/537.7, 689, 506, 539, 573.4, 573.7, 576, 340/686.1, 825.19, 539.12, 531
See application file for complete search history.

(56) References Cited

U.S. PATENT DOCUMENTS

| | | | |
|---|---|---|---|
| 4,510,350 A * | 4/1985 | Wagner et al. ................. 379/38 |
| 4,814,751 A | 3/1989 | Hawkins et al. | |
| 4,829,285 A | 5/1989 | Brand et al. | |
| 5,519,380 A | 5/1996 | Edwards | |
| 5,923,253 A | 7/1999 | Anastasiou | |
| 5,963,130 A | 10/1999 | Schlager et al. | |
| 6,307,481 B1 | 10/2001 | Lehrman et al. | |
| 6,433,690 B2 * | 8/2002 | Petelenz et al. ............ 340/573.1 |
| 6,501,386 B2 | 12/2002 | Lehrman et al. | |
| 6,661,347 B2 | 12/2003 | Lehrman et al. | |
| 6,703,939 B2 | 3/2004 | Lehrman et al. | |
| 6,788,206 B1 | 9/2004 | Edwards | |
| 6,864,796 B2 | 3/2005 | Lehrman et al. | |
| 7,095,331 B2 | 8/2006 | Lehrman et al. | |
| 7,150,048 B2 * | 12/2006 | Buckman .......................... 2/465 |
| 7,411,510 B1 * | 8/2008 | Nixon ......................... 340/573.1 |
| 7,567,200 B1 * | 7/2009 | Osterweil ....................... 342/28 |
| 2002/0052159 A1 * | 5/2002 | Eguchi ............................ 441/80 |
| 2006/0224048 A1 | 10/2006 | Devaul et al. | |
| 2006/0252999 A1 | 11/2006 | Devaul et al. | |
| 2006/0276714 A1 * | 12/2006 | Holt et al. ...................... 600/481 |
| 2006/0282021 A1 | 12/2006 | Devaul et al. | |
| 2007/0063850 A1 | 3/2007 | Devaul et al. | |
| 2007/0295713 A1 | 12/2007 | Carlton-Foss | |
| 2009/0121881 A1 * | 5/2009 | Fredriksson et al. ...... 340/573.4 |

\* cited by examiner

Primary Examiner — Daniel Previl
(74) Attorney, Agent, or Firm — Devine, Millimet & Branch, P.A.; Paul C. Remus; Kimberly A. W. Peaslee

(57) ABSTRACT

A fall detection system includes a wearable monitoring device that monitors the movement of a person. The device monitors a sensor and detects variation from the normal range and duration thereof. The system determines whether the wearer has fallen through an algorithmic analysis technique using parameters to evaluate the accelerations and timings of the events that comprise a fall. If the combination of the timing and variations from the normal ranges are sufficient as compared to preset thresholds, a fall report will be generated. The wearable device optionally allows qualified professionals to adjust or customize the parameters to optimize the evaluation to the requirements of particular users or classes of users. The wearable device generally transmits data and alerts over a short distance to a console or over a long distance using a connection to a long-distance back haul communication system such as cell network or internet or both. The device thus transmit data and alerts to a call center or other designated location.

17 Claims, 12 Drawing Sheets

METHOD AND SYSTEM FOR FALL DETECTION

CROSS REFERENCE TO RELATED APPLICATIONS

The present application claims the benefit of Provisional Patent Application No. 60/873,108 filed Dec. 5, 2006, which is incorporated herein by reference.

BACKGROUND

Falls represent one of the most fearsome risks for the elderly. At the very least a fall represents the onset of loss of independence. At the other extreme, a fall initiates life's endgame, lasting anywhere from hours to a few months, depending on circumstances and severity. For example, even if an elderly person is using the most sophisticated available technology, if the person falls and goes unconscious, the person may lie in one place for minutes or hours until death comes.

Likewise, particularly for those suffering from acute or chronic illness, including various forms of heart and circulatory disorders that yield dizziness, or for those who are at elevated risk for illness or injury, including those who suffer neuropathies such as tingling and loss of sensation in the feet and legs, the automatic detection and automated reporting of life-threatening falls, could mean the difference between life and death.

Fall detection is desirable as part of care programs for the elderly, the infirm, and for people with certain chronic or acute physical or psychiatric disorders, in some cases because they are taking psychotropic medications that can cause dizziness and disorientation. A fall may provoke an acute medical crisis. Particularly among the elderly or those who are hospitalized, having fallen recently is commonly accepted as a significant risk factor for additional falls, which may yield injury and declining vigor and health.

One conventional fall detection device has the user press a call button to indicate a fall. Other conventional fall detection devices send a signal when the person's orientation has changed to a horizontal position. A third type of detection device uses a sensor, such as an accelerometer, and forwards the data to a station, such as a nursing station, where a person interprets the data to determine if a fall has occurred. A fourth type of detection device uses a 60 Hz sampling rate with a fast Fourier transform and classifier to discern the near-instantaneous pattern of contact with a horizontal surface during a fall from the patterns of other motions.

SUMMARY

It is recognized that conventional fall detection systems have numerous false positives or false negatives in their determination of a fall if based on a person taking an action after a fall or on the physical orientation of the person. Likewise it is not desirable or likely possible to have a person monitor data continuously to determine if a person has fallen.

In contrast to conventional detection systems, the embodiments of the invention are directed to a fall detection system that has the ability to monitor one or more sensors and detect when the output changes from the normal range. The system monitors both the time and sensor output. If a sequence of logical conditions is satisfied, a fall report will be generated. Continuing monitoring without entering the logic sequence leading to a report indicates that the sensor is noting conditions in a certain range. The system does not require the sensor to indicate that the user is in a horizontal position. Therefore, the improved detection system of analysis of the combination of time and variation from the normal range will have a higher rate of reporting true falls without false positives than the conventional system.

The fall detection system measures accelerations during the events of the three phases of falls. As a result, the fall detection system can be worn while engaging in any of the full range of daytime and night-time activities while minimizing false positives and false negatives. The fall detection monitor device is a body-worn or implanted device having sensors, microelectronics, embedded processors running statistical smoothing algorithms as well as deterministic and statistical algorithms, and digital or analog communications for the remote monitoring of falls. The device is packaged in a manner that is as comfortable and non-invasive as possible, and puts little additional physical or cognitive burden on the user. It is robust and reliable, small and lightweight, unobtrusive and accurate.

In one arrangement, a wearable device for a remote monitoring system is positioned on the body of a person. The wearable device includes a data receiver to receive sensor data transmitted from at least one sensor positioned on the person. An analysis module of the wearable device takes the sensor data as input and analyzes timing and the sensor data to generate a report. The wearable device has a transmitter to communicate the report to an external device. These parts of the device can all be housed in one assembly, or they can be distributed among one or more assemblies.

In one arrangement, the analysis device of the wearable device has an algorithm with one or more stored parameters. The analysis device uses the parameterized algorithm to interpret the sensor data. The parameters include acceleration thresholds, geometric thresholds, and timing thresholds.

In one arrangement, the analysis device is analyzing data in relation to a fall condition and the one or more stored parameters. The stored parameters each have a default value adjustable by qualified professionals to characterize the fall condition for individual people or classes of people.

In an arrangement, the analysis device provides an indicator of the relationship of the sensor data with the data of the at least one stored model. For example, the analysis device uses reported values to indicate how much the accelerometry output data matches or deviates from the parameters used by the algorithm.

In an arrangement, the wearable device has an accelerometer and an impact detector as sensors.

In an arrangement, the wearable device has a data diary, data storage, for retaining collected data from the sensors about falls and near falls to facilitate adjusting the parameter settings for the user. In addition, the data storage retains outputs from the algorithms.

In an arrangement, the wearable device for a remote monitoring system has a data receiver to receive data from at least one sensor positioned in the device. The wearable device has a parsing device to chunk through the datastream from the data receiver to determine the values of the acceleration and impact in three dimensions. An analysis device takes the data as input and includes a set of parameters. The analysis device with an algorithmic function operates on the received data to determine if the person has had a fall on the basis of the truth value of one or more conditions. A transmitter transmits a fall report to an external device.

In one method of determining if there has been a change in a person's physical situation, at least one sensor carried on the person is sampled. An algorithm of the wearable device detects when the sensor indicates a change from a normal range to a second range. The wearable device continues to sample the sensor to determine if the sensor is outside of the normal range for over a specified period. A signal is generated regarding change of situation if specific criteria are met.

In one arrangement, the method detects when the sensor indicates a change from the second range to a third range. The device continues to sample the sensor to determine if the sensor is in the third range for over a specified time period prior to generating a signal regarding change of the position.

In one method of determining if there has been a change in a person's physical situation, at least one sensor carried on the person is sampled. An algorithm of the wearable device detects when the sensor indicates a change from a normal range to a second range. The wearable device continues to sample the sensor to determine if the sensor is outside of the normal range for over a specified period. A signal is generated regarding change of situation if specific criteria are met.

In one arrangement, the specific criteria are at least one sensor recording a negative acceleration over a minimum threshold. The generated signal is communicated to an external device.

In one arrangement, the analysis device of the wearable device includes at least one stored parametrized data structure of the events characteristic of a fall wherein the analysis device uses the at least one stored model to analyze and compare the sensor data. In another arrangement, at least one stored model holds default values for the parameters and the parameters as adjusted by a qualified professional. Accordingly, the remote monitoring system can determine whether the wearer of the wearable device has fallen by comparison to events characteristic of a fall. The wearable device therefore is not confused by other types of movements such as merely reclining, or bumping against a wall or doorknob.

In one arrangement, the wearable device provides indicators of whether the sensor data falls within the domains of expected data of the at least one parametrized data structure for a fall. These indicators enable the electronic logic of the device, and an entity such as a call center or caregiver, to interpret the comparison between the actual sequence of events and the parametrized data structure.

In one method of sensing whether a person has fallen, the device receives data from a sensor located on the body of the person. The datastream from the data receiver is parsed to determine the values of the acceleration in three dimensions. The data is analyzed using an implicit set of conditions characterizing one or more events with stored values that are compared to the accelerations in the datastream. A fall report is generated in response to the analyzing step.

In one arrangement, the fall report is transmitted to an external device. The data is received from a plurality of sensors located on the body of the person. In one arrangement, the data received from the sensor or sensors is transformed to obtain values to logical conditions and variations to those values and conditions to indicate a particular condition of the person. The analyzing of the transformed data uses stored parameters, whether they be the default parameters within the device or the parameters set by a qualified professional.

In one arrangement, the logical evaluation of at least one condition is achieved, and at least one statistic is calculated to indicate the sureness with which the condition evaluates to true or false based on the data and the parameters. The data is made available for caregivers to determine the details of the candidate fall event.

In one arrangement of a fall detection system, the fall detection system has a wearable device and a console. The wearable device has at least one sensor and at least one stored set of parameters characterizing how to interpret potential fall events. The wearable device is able to detect through algorithmic analysis of sensor data with regard to the parameters whether a wearer of the wearable device has fallen. The wearable device has a transmitter to transmit a report of whether a fall has been detected. The console or server has a receiver to receive a report from the wearable device. The console or server then transmits an alert, and optional additional information, to one or more triage points for care response in response to the report.

In one arrangement, the transmitter in the wearable device is a short-range transmitter. In another arrangement, the wearable device transmits the report to the console over the wireless local area network. In another arrangement, the wearable device transmits the report to the call center over the Internet.

In one arrangement, the console includes a mobile power source whereby the fall detection system is usable away from a fixed location. In an arrangement, the console is a cellular telephone. The console has a locator device.

In one arrangement the wearable device monitors the remaining life of the battery, indicating when the available remaining battery power falls below a certain level, indicating that the battery will soon require changing or recharging.

In one arrangement the wearable device performs a periodic or on-command self-check to determine if the device and individual components are functioning properly, and reports the results of that check to at least the call center.

BRIEF DESCRIPTION OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

An improved fall detection system has the ability to monitor a sensor and detect when the sensor changes from the normal range. The system monitors both the time and variation over the entire range of motion. If the combination of the length of time and variance outside the normal range is within preset thresholds, a fall report will be generated. The system will also generate a fall report if the combination of time and variance from the normal range is below the preset threshold, but continuing monitoring indicates that the sensor is noting conditions in a certain range. The system does not require the sensor to indicate that the user is in a horizontal position, or tilting, or accelerating the tilt at any particular rate. Therefore, the improved detection system of analyzing the combination of time and variation from the normal range will have a higher rate of reporting true falls without false positives than conventional systems.

Figure 1:
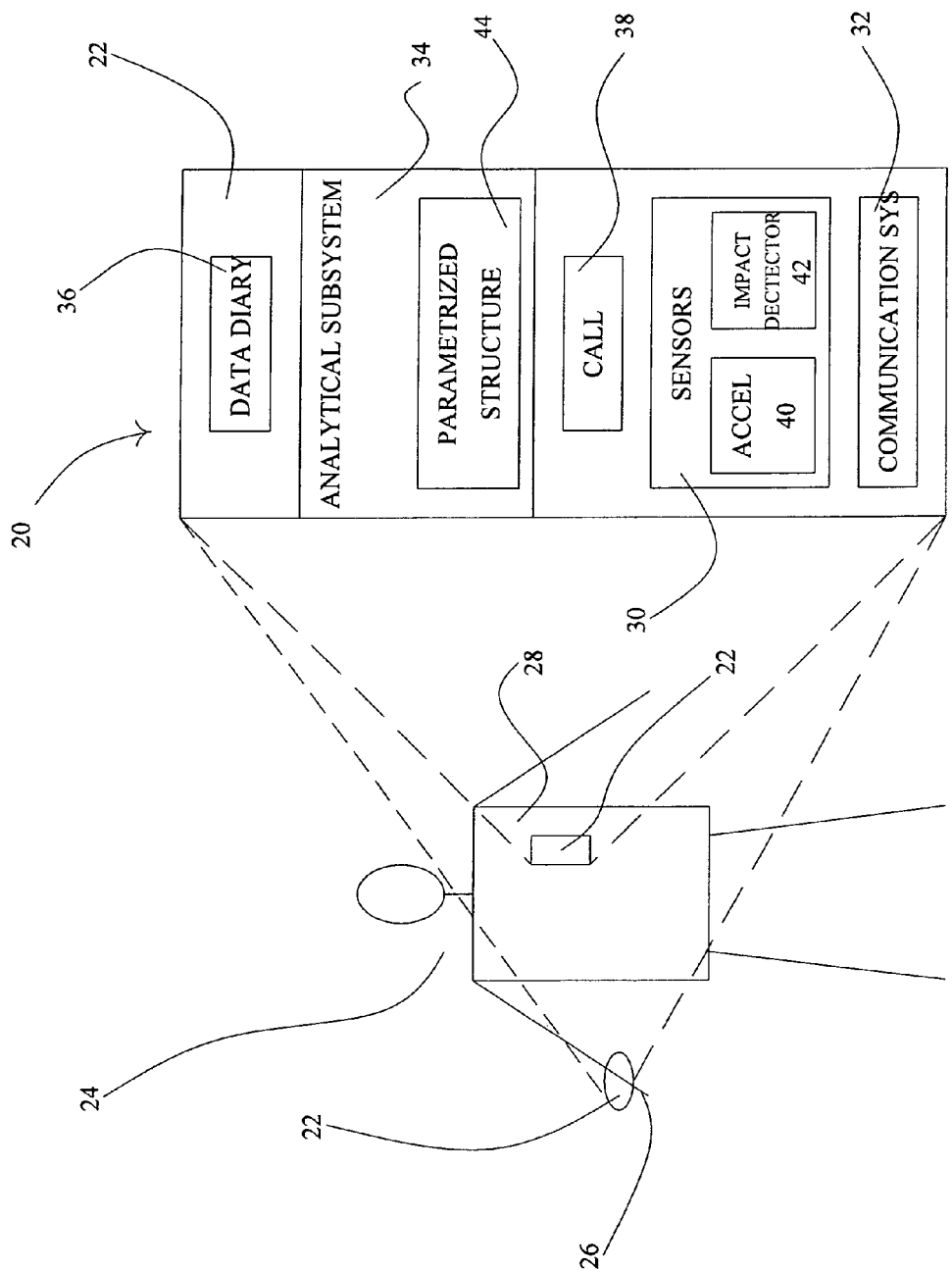
FIG. 1 is a schematic of a person wearing a wearable fall detection monitor device of a fall detection system.

FIG. 1 shows a schematic of a wearable fall detection monitor device 22 of a fall detection system 20 located at two possible locations on a human FIG. 24. The human figure representation 24 is shown wearing a monitor 22 on the wrist 26 and a monitor 22 in proximity to the chest 28. In the arrangement described, the user 24 has a single fall monitor device 22 of the fall detection system 20 located on the wrist 26. It is recognized that multiple fall monitor devices 22 can be used. The fall detection monitors 22 can be located on other positions on the user, typically located above the user's waist. The fall monitors can be in various styles including a pocket version, a version clipped to a belt, a version attached to the head, or a pendant version. The parameters described below may be different for each of these placements.

The wearable fall detection monitor device 22 on the wrist 26 contains a sensor system 30 and a communication system 32. In addition, dependent on the style of the fall monitor 22, the monitor 22 can include an analytical subsystem 34, a data storage system 36, and a call button 38. The sensor region can include multiple and varied sensors including an accelerometer 40 and an impact detector 42.

In the arrangement shown, the wearable fall detection monitor device 22 has all the components recited. It is recognized that in some arrangements that certain components will be on other devices 22. For example, if there are multiple wearable fall detection monitor devices 22, a call button 38 may be located only one device.

An impact detector 42 is an accelerometer or a body-linked microphone that detects and interprets the sounds, or rapid accelerations and decelerations that occur on parts of the body remote from the site of impact when an impact occurs, or the sound produced by the shock waves from impact. One such example is the device as developed by Natick Labs in the Future Force Warrior Project that detects shock waves from bullets impacting on the human body and that carry through the bones and viscera.

In order to understand how to determine if a fall has occurred, a brief discussion of falls is provided. Falls can happen in a number of ways. Falls vary according to such factors as the direction of the fall, the flexure of the body during the fall, the surfaces against which the body impacts during the fall, how the body comes to rest, and the nature of the reaction of the person to the fall. Examples include a collapse downward in free fall; a topple forward, backward, or sideways; a collapse of one leg; a trip and fall; a slip and fall; a misstep and fall, particularly on stairs. Falls also vary according to such cognitive factors as whether the person is aware of the beginning of the fall or not, whether the person is aware of the cause of the fall or not, and how the person reacts to the fall. In a fall, a person's body may come to a quick equilibrium upon contact with a floor, or it may take several seconds to reach equilibrium, as when the fall results in sliding down a flight of stairs. Falls vary according to whether the person is conscious or not at the conclusion of the fall, including what class of concussion the person may suffer. Many falls are associated with medication, with substance abuse, or with inability, so that even when people who have fallen are conscious, they may not be able to take charge of their situation.

Principles of classical physics can be used to understand and characterize falls, and to simplify the treatment of falls. When people collapse, they go into free fall until some combination of body parts impacts the ground and they reach a stable equilibrium. To gain an approximate understanding of the dynamics of this kind of fall, one can assume by way of an example that the equilibrium point is reached when the buttocks hit the ground.

Figure 2:
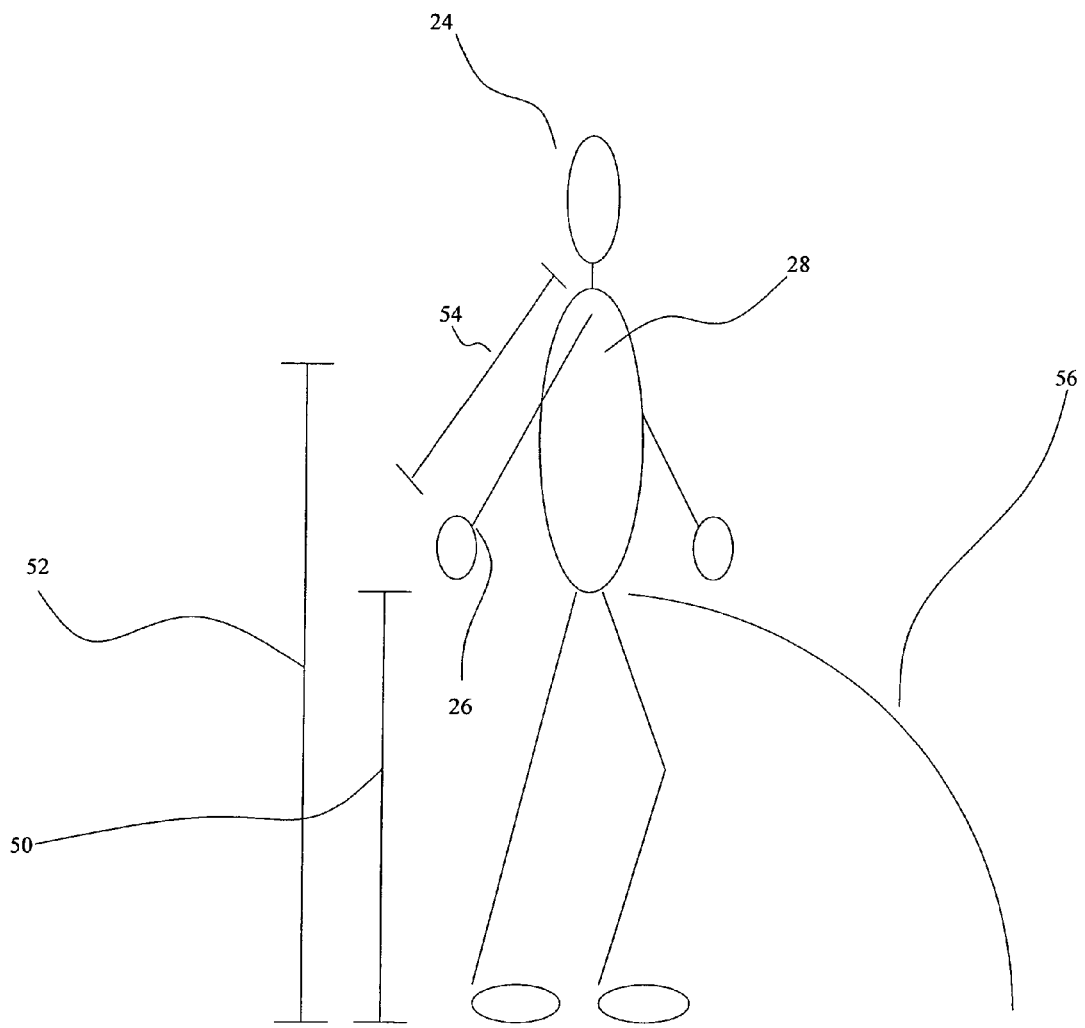
FIG. 2 is a schematic diagram of a person walking, with key body dimensions for teaching the structure of a fall.

Referring to FIG. 2, dimensions are schematically represented for the human figure representation 24. The height of the hip of the human FIG. 24 above the ground for a standing/walking human is represented by line 50. The height of the fall monitor 22 above the ground on the chest 28 for the standing human 24 is represented by line 52. The distance of the fall monitor 22 on the wrist 26 from the fall monitor 22 on the chest 28 is represented by line 54.

If the person weighs 200 lbs and has hip joints located at the height represented by the distance 50 of about 36 inches, then the fall will take a little more than 0.4 seconds until impact. Velocity at the point of impact is almost 14 feet per second, and the resulting momentum of 280 ft-lb/second will be brought to zero with a simple to complicated impact with the ground. During impact the tissues between the skin surface and the bone structures are rapidly compressed, buffering the fall. Taking a typical tissue thickness of 0.25 inches, the impact takes about 2 one-thousandths of a second. Before the fall, the person is in a standard 1 G gravitational field. During the free fall, the person is still in a 1 G field, but an accelerometer will read 0 G because of the free fall. During the time of the impact the localized acceleration spikes to a very high multiple of the standard gravitational field (G's), although the value of acceleration measured by an accelerometer elsewhere on the body (such as on the torso, chest 28, or wrist 26) is generally lower because the body dissipates the impact energy as if it were a bag of connected bones or a complex pendulum-like object. The very high multiple of the standard gravitational field (G's) will be in the opposite direction, reading as negative G's, the more exact meaning of which will be addressed below.

Similarly, when people topple, they go into a modified free fall with an acceleration that starts near zero and increases to 1 G near the time of impact, when some combination of body parts impacts the ground. To gain an approximate understanding of the dynamics of this kind of fall, one can assume that the equilibrium point is reached when the hip hits the ground. Still referring to FIG. 2, the vertical distance fallen will again be the distance represented by line 50, although the path is not substantially straight down, but rather in a curved path approximated by a quarter-circle represented by path 56, so the distance traveled is the distance represented by line 50×π/2 radians.

If the person weighs 200 lbs and has hip joints at about 36 inches then the fall will take between 0.4 seconds and well more than 1 second until impact, depending on the details of the fall. Velocity at the point of impact is almost 14 feet per second, and the resulting momentum of 280 ft-lb/second will be brought to zero with the simple to complicated impact with the ground. During impact the tissues between the skin surface and the bone structures are rapidly compressed, buffering the fall. Taking a typical tissue thickness of 0.25 inches, the impact takes about 2 one-thousandths of a second. Before the fall the person is again in a 1 G gravitational field. During the free fall the person is still in a 1 G field, but an accelerometer will read a decreasing function ranging from 1 G down to 0 G just prior to impact. During the time of the impact the localized acceleration spikes to a very high multiple of G's, at times enough to shatter a lean healthy hip if the impact is directly on the hip joint, although once again the value of acceleration measured by an accelerometer elsewhere on the body (such as on the torso or wrist) is made lower because the body dissipates the impact energy as if it were a bag of connected bones or a complex pendulum-like object.

Figure 3:
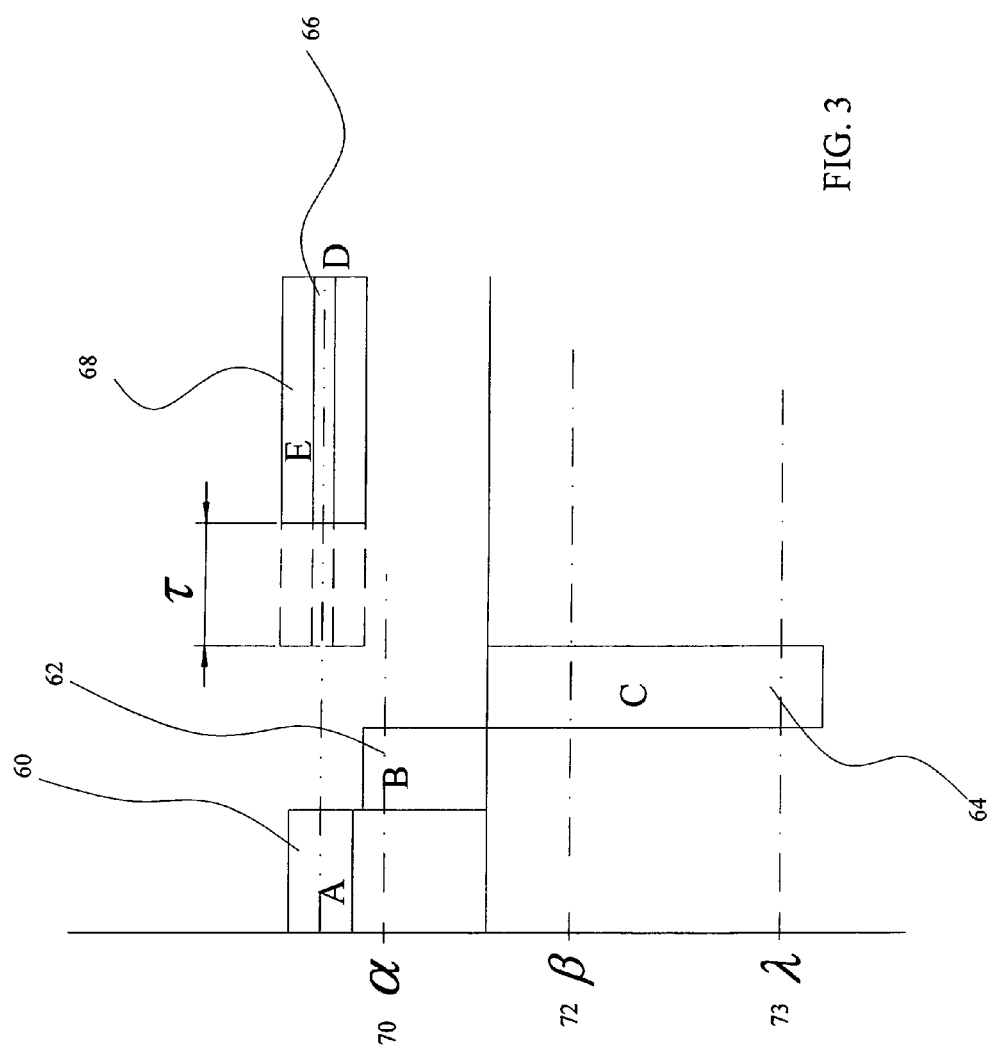
FIG. 3 is a diagram of the structure of fall candidates.

With recognition of the anatomy of a fall, the pattern of variations of the resultant accelerations the sensor detects is described. Referring to FIG. 3 shows a series of conditions that occur and the fall detection system 20 senses and interprets. Box 60, represents Condition A, that of the normal condition, with the long horizontal line between α and β representing the time axis and the intersection with the vertical axis being at approximately 1 G. A second condition is represented by box 62, Condition B, that of the accelerometer system 30 determining a decrease in G's for a minimum period of time. As indicated in greater detail below, the actual G level sensed by the sensor that is required to satisfy the condition can be adjusted, but a G force that deviates from 1 G just slightly such as 0.92 G's would not meet Condition B because it could too frequently be produced in normal motion and therefore would be too likely to initiate the logical sequence for a candidate fall, thus wasting fall monitor resources and potentially admitting a false positive result.

Still referring to FIG. 3, the fall detection system 20 monitors the sensor system 30 to determine if negative G's (meaning that the force vectors implied by the accelerometer measurements before and during the impact are within π/2 radians of directly opposite) are sensed to signify the hitting of a hard object, such as the floor. Box 64, Condition C, represents such a condition. The fall detection system 20 continues to monitor to determine what occurs after the negative G condition. If the sensor system 30 monitor returns to 1 G with only minor deviations from 1 G, the user is in state Condition D. If the sensor system 30 monitor returns to 1 G but has deviations from 1 G in excess of a certain percentage, for example 80 percent, the sensor is in stage Condition E, represented by box 68. The fall detection system 20 monitors by deviations from normal condition, but also monitors by time to determine if a fall has occurred. Such deviations can be evaluated as significant either by non-statistical analytic formulas such as those expressed above, or by statistical techniques such as those of Walter Shewhart working with control charts based on the stored motion patterns of the particular individual or of classes of individuals. *Understanding Variation: The Key to Managing Chaos* by Donald J. Wheeler (Knoxville Tex.: SPC Press Inc., 1993) is incorporated herein by reference.

Figure 4:
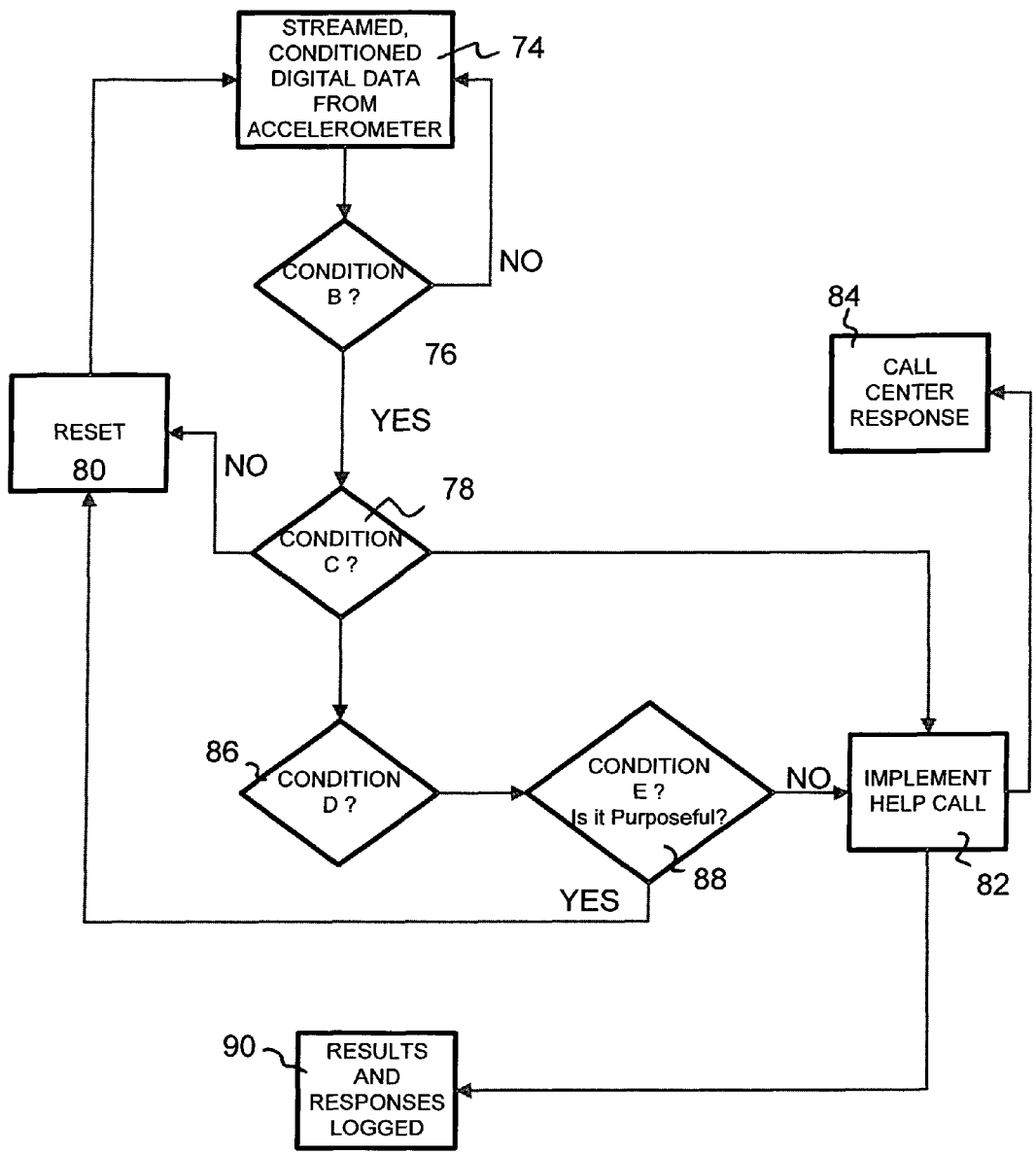
FIG. 4 is a diagram of the analysis algorithm and triggering of an alarm at a call center according to principles of the invention.

Referring to FIG. 4, an algorithm for signaling a fall condition is shown. The analytical subsystem 34 of the fall monitor 22 of the fall detection system 20 receives a stream of conditioned data 74. This streamed, conditioned data 74 is transmitted to a first comparator 76 section of the algorithm, which determines the value and direction of the acceleration. If the value present does not reflect the characteristic of Condition B, box 62 in FIG. 3, then the algorithm continues to read the accelerations and takes no further action. If the value presents among the values characteristic of Condition B, box 62 in FIG. 3, then the sequence for a possible fall is initiated. The analytical subsystem 34 is monitoring both values from the sensor system 30 and the time of each. If condition B is fully met and evaluates to TRUE, then the algorithm continues to read the data stream and moves on to a second comparator 78 to determine if the value of logic condition C, box 64 in FIG. 3, is met. In one arrangement, condition C, has three paths. If the value does not present in the domain characteristic of Region C, then the algorithm continues to read the accelerations and takes no further action other than returning to a reset, box 80, and back to the beginning of the logic sequence.

If the accelerometer output presents values characteristic of Condition C, the sequence for a possible fall continues. Note that the lower extreme of the domain for Condition C ranges from the adjustable value β, with default value −1 G, to values that can be −150 G or even lower. If the sensor has determined that the measured value is less than the adjustable threshold level, X, with default value such as −4 G, represented by line 73, Region C, then optionally the fall detection system 20 immediately initiates a call, as represented by a box 82 to a call center 84.

If the accelerometer output presents values less negative than the threshold value β, then the algorithm continues to read the accelerations and takes no further action other than returning to a reset, box 80, and back to the beginning of the logic sequence.

If the accelerometer output presents values in the inclusive interval between the upper threshold value β, and the lower threshold value λ, with β represented by line 72, and λ represented by line 73, in FIG. 3, Condition C is fully met and evaluates to TRUE. In this case the algorithm continues to read the data stream and moves on to another comparator 86 to determine whether the value of logic condition D, box 66, in FIG. 3 is met. As described elsewhere, there is a settable time delay, τ seconds, between the end of domain C, box 64, and the beginning of region D, box 66, on the graph. If the values of the accelerometer readings are within the upper and lower values for the set period of time for region D on the graph, then Condition D, box 66, is met, and the sequence immediately initiates a call, as represented by a box 82 to a call center 84. Note that region D, box 66, is a domain much more closely limited around 1 G than the limits for region E, box 68, which would characterize various normal activities such as also are characterized in Domain A.

Still referring to FIG. 4, a data buffer is logging new information and overwriting old information continuously so that when Condition B is met, data is already logged in a data diary 90 beginning at least ten seconds prior to the onset of the event sequence. Optionally, the data buffer, logging information continuously, also stores similar data to the data diary when Condition C or Condition D is met, and data is logged in a data diary 90 beginning at least ten seconds prior to the onset of the event sequence. The use of the data diary 90 is described in further detail below.

If the characteristic of condition E, box 68 of FIG. 3, is met, the fall detection system 20 optionally interprets the user 24 as moving and able to signal manually, if desired, that a fall has occurred. The fall detection system 20 returns to the reset, box 80, and back to the beginning of the logic sequence.

If at any point the user manually initiates and makes a successful call, then the automated fall detection process continues in order to record information about the fall sequence, but does not initiate a redundant call. While the at least one set of conditions is shown to trigger an automatic call, those skilled in the art will recognize that alternative conditions could be used as the criterion to trigger an automatic call for help, such as the requirement that only two conditions, or a fourth condition be met in order to trigger an automatic call for help. Similarly, there are alternative default values that can be used, and additional conditions that can be used, without materially changing the inventive device.

Figure 5:
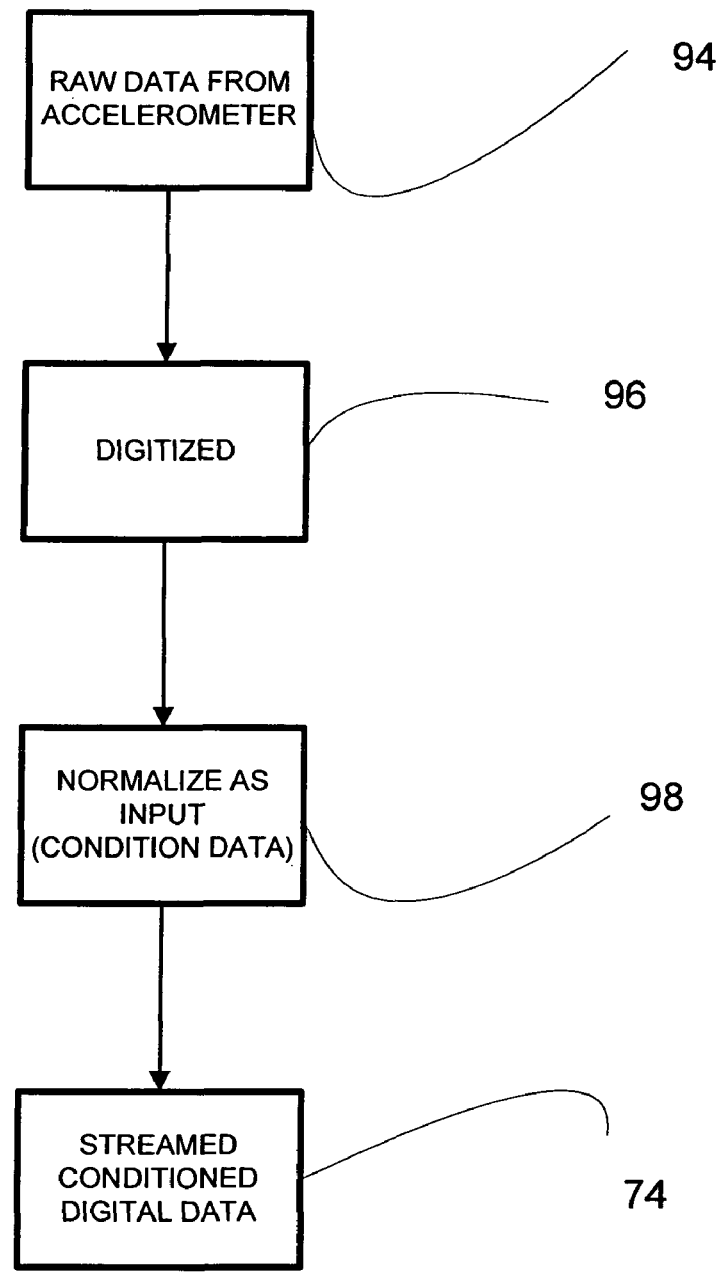
FIG. 5 is a diagram of the preprocessing to prepare data for the analysis algorithm.

Referring to FIG. 5, a schematic of the preprocessing to prepare the data for the analysis algorithm is shown. The sensor system 30 such as the accelerometer 40 is sampled at a sampling rate, such as 10 to 20 samples per second or more frequently, corresponding to one or two samples every tenth of a second or more frequently. If the raw data from the accelerometer 40 is in analog form, as represented by a box 94, the data is digitized as represented by a box 96. The data is then transmitted in digital form to the signal conditioner, represented by box 98, where it is smoothed and converted into a form acceptable for input into the software program on the microcontroller. The smoothed data of the sensors 30 is streamed as conditioned data 74 described with respect to FIG. 4.

It is recognized that the smoothing and conversion can be readily implemented in either hardware or software. Therefore this step of an arrangement could be located logically either in FIG. 4 or FIG. 5.

With an overview of the fall detection system 20, a first scenario is described to further exemplify the fall detection system 20 and the fall monitor 22. During normal activity, the sensor 30 reads approximately 1 G. The variation from 1 G is dependent on the person's activity, such a sitting, walking, running, or playing a sport. The normal range may correlate to the age and lifestyle of the user and be adjusted as described below. It is recognized that for certain activities the accelerometer will read both close to 0 G's and negative G's for short periods of time such as during playing basketball. In addition, there will be periods where the sensor 30 deviates only slightly from 1 G. The fall detection system 20 in the analytical subsystem 34 interprets the conditioned sensor 30 outputs to determine if a fall has occurred and if a call should be initiated, as represented by box 82 in FIG. 4.

There are some key indicators that the fall detection system 20 through its analytical subsystem 34 determines whether a fall has taken place. The numbers given here are merely examples and can be adjusted as described below. Referring to FIG. 3, the accelerometer reading decreases to a level below the threshold level α, line 70, for example somewhere less than 0.5 G's for a time period of 0.2 seconds or more.

This is followed by negative G's (meaning in a direction approximately opposite to the direction of acceleration shortly prior to impact, as discussed earlier) during impact which follows this earlier changed acceleration value. (Since this range will vary, it needs to be an adjustable parameter in the device, as discussed elsewhere.) Third, there is a period of substantial motionlessness, the duration of which the fall detection system 20 uses in determining whether the person who fell is collecting themselves and checking to see if everything in the first approximation is still working, or if the person is too badly injured to move. (Since the characteristics of this range will vary, it needs to be an adjustable parameter in the device, as discussed elsewhere.) In one version, the fall detection system 20 uses as one of its assumptions that persons who move are sufficiently conscious and able to trigger a manual alarm indicating that they need help. It also assumes that such able people may take from a few seconds to at most a minute to assess their condition while substantially motionless, but that after this time of preliminary assessment, they will begin to move. People who are sufficiently disabled by a fall will continue substantially not to move during the time window designated by the default boundaries or the adjustments made to them by qualified professionals. In another version, the device would use a classifier or other technology to detect whether the person had arisen and begun to walk, or otherwise begun to perform normal activities that would indicate that the fall had not been sufficiently serious to warrant calling emergency personnel for assistance.

During normal conditions, the fall detection system 20 registers small harmonic variations within the zone of accelerations for normal functioning (Condition A, Box 60 in FIG. 3). The arm with the wearable fall detection monitor device 22, as seen in FIG. 2, will swing during walking, yielding an oscillation of acceleration around the central value of about one G. Occasionally idiosyncratic events will occur. For example, the wrist may hit an obstruction such as a doorknob, yielding a very brief impact, much briefer than those for voluntary arm movements, with very high values for acceleration, but when the context, direction, and time of the acceleration are considered or these impacts are smoothed, and the fact that the motion returns to that of the zone for normal functioning, they do not register as indicators for a fall.

If the fall detection system 20 notes a reduction in the positive value of acceleration to the condition B, Box 62 in FIG. 3 for a period of about 0.2 seconds or longer, the analytical subsystem 34 will continue to monitor the sensor system 30 to determine if the next condition is met. The condition B will not be identical each time and the actual change in G's and timing will depend on the distance and type of fall. For free fall, the accelerometer reading will be zero G's. For a toppling fall with no flexure of the body, the value will decrease monotonically to zero G's from approximately one G. For falls that are a combination of these falls, the same condition will be met, although with different evolution of the details. Even for more complex falls, toward the end of the falls, people tend to move their wrists toward the ground to help break their falls, so that very shortly before impact the accelerometer reading at the wrist is likely to be zero G. Thus, for falls of this type there will be a period of at least approximately one or two tenths of a second with accelerometer readings less than α, as represented by the condition B, Box 62 of FIG. 3. The threshold parameter, α 70 can also be adjusted by the physician or other qualified person to characterize the falling condition for this individual.

As indicated above, very brief impulses, such as would happen if the device struck a doorknob during the fall, would be smoothed out of the trace or would otherwise not influence the determination of whether there is a fall. That is, even if the impulse were not smoothed out of the accelerometer trace, there would be no low-G event just prior to the impulse, and the impulse the sensor system 30 detects would not yield a call for help, because the person would continue to move normally, indicating that a dangerous fall had not occurred. Thus, condition B, for the falling condition, is TRUE when the smoothed accelerometer reading is less than α for a minimum period. It is FALSE when it is outside this region because it is greater than α, as represented by Box 62 of FIG. 3. (There is a default value for α, such as 0.5 g. If the qualified professional sets the value higher, there is a greater likelihood that the fall-in-progress condition will be met, yielding fewer false negatives and more false positives. If the qualified professional sets the threshold parameter a lower, there is a greater likelihood in the direction of a fall having to be a free fall for the device to consider a fall to be occurring.)

In the third stage of a fall, the person's body contacts one or more horizontal, vertical, and otherwise oriented surfaces. During a period ranging from approximately 0.1 seconds or the minimum length of time that the device can discern, there are one or more short accelerations representing the rapid deceleration of the body. The motion may also include horizontal accelerations as the body and its parts impact or bounce off vertical surfaces. It is possible that one second or more will be required for the body to come to a stop, such as a situation wherein the person 24 falling results in the person sliding down a series of steps. This type of fall is different from a free fall of several feet to a hard surface which results in rapid deceleration, high negative acceleration, wherein the sensor is clearly above the threshold parameter β 72 of FIG. 3. The sliding down a series of steps does not result in such a high negative acceleration, but does result in a longer time period of negative acceleration. If the fall is a minimum distance and the impact is cushioned, such as a short person with an ample buttocks falling backwards onto a well padded floor, the deceleration will may be a fraction of 1 G.

This, for example, could be a person slipping and falling while running. The person puts out their arm that has the fall monitor 22, in an attempt to control the fall, resulting in the fall monitor 22 experiencing a different G force on the wrist 26 than what would be measured on the chest 28 in that there is relative motion between the different parts of the body at these locations. If the person falls either forward or backward and the monitored hand contacts the pavement directly, then it is thrust in approximately the reverse direction by the impact. The deceleration of impact has a magnitude significantly greater than 1 G. In the less likely event that the person's wrist is held so that it moves exactly with the body, the deceleration will occur either by delayed impact with the pavement or body, in which case there is a sharp impact and change of direction, or as a result of muscle and tendon strength, in which case the magnitude of the deceleration is again significantly greater than 1 G. Thus this motion somewhat shifts the motion domains for Condition B and Condition C in particular, increasing the acceleration downward during portions of the fall and often increasing the deceleration at impact, but the effect is small and the condition evaluates substantially the same.

In another scenario, an elderly person enters the bathroom during the night and begins a topple fall to her left without knowing it. Partway down, she realizes what is happening and grabs her portable IV stand in an attempt to arrest her fall. If her wrists have accelerated upwards and to the side rapidly enough, Condition B will not have not been met yet and the device will continue its monitoring without proceeding to Condition C. The stand briefly provides assistance and then topples with her. Condition B has still not been met, and even if this grasping might produce an event that satisfies Condition C, the device does not evaluate whether it does. The topple fall continues, and in the final approximately 0.2 seconds Condition B evaluates to True. As above Condition C subsequently evaluates to TRUE based on the impact at the bottom of the fall. Then if she does not continue to move enough after the fall, the device evaluates Condition D as TRUE and sends an alert to the call center. If she does continue to move, the device in normal mode leaves it for her to initiate a call for help. Consider, however, if the falling person had a very slow reaction time, therefore what the sequence would have been if the person had been reaching out to grab some object such as her IV just as her torso hit the floor or a wall. In this case the wrist monitor would be moving or even accelerating toward the object and away from the direction of the fall. In such circumstance the wrist monitor will still in almost all cases provide a correct evaluation of the first two events in the fall, but it is possible in some circumstances that it might not register a net falling acceleration sufficient to set Condition B to TRUE. The way to avoid this false negative is to have two monitors, one on the wrist, the other on the body, and set a hub to initiate a call for help if either of them registers a fall. Thus, it is recognized that the device as designed might be thought of as a tool that enables qualified people to assemble a detector of all possible falls, rather than as a device that guarantees detecting all possible falls, and all such composite fall detectors would be considered within the spirit of this invention.

In yet another scenario, an elderly person misses a step at the top of a flight of stairs and falls on her buttocks. The initial descent triggers Condition B, the impact triggering Condition C if she comes to an immediate rest at the top of the stairs. Whether Condition D is satisfied, and a call placed for help, depends on her motion after the fall. In the case that she slides bumping down the stairs, she may suffer bruises but not bone damage. She may be shaken and disturbed enough to trigger a call for help, but this is not sufficient to warrant an automatic call for help. Consistent with this, the initial impact may be distributed over those many bumps down, and Condition C never satisfied. However, if Condition C is triggered, then it is important that the delay until evaluation of Condition D be sufficient so that the path down the flight of steps is consummated. Then if Condition D evaluates to TRUE at the bottom of the steps, an alert is sent to the call center, and if it evaluates to False, then no automatic message is sent.

In another scenario, if a person falls out of bed, then he will be in free fall for the more than 0.2 seconds until hitting the ground. During this free fall Condition B will evaluate to TRUE, unless the bed surface is so low to the ground that the 0.2 to 0.4 second time window cannot be met, in which case there is unlikely to be a serious injury and the condition B still evaluates to False. At impact Condition C will evaluate to TRUE. Then if the person continues as motionless, Condition D will evaluate to TRUE and an alarm message will be sent to the call center.

In another scenario for understanding the avoidance of a false positive, a person performs an overhead serve in tennis or squash, the sweeping motion of the arm can satisfy the condition B, and the impact with the ball may satisfy condition C. However, the wrist monitor will remain in motion as the point is played out, so that condition D does not evaluate to TRUE, and the device will not send an alert message to the call center. Similarly, a person may slide out of a chair, with the distances and contacts such that the wrist never attains the accelerations over time required to satisfy Condition B. This would be a correct result for potential damage to bones in the torso and members, but the person could still suffer a concussion as a result of the head suddenly dropping from the level of the chair to a hard floor, particularly if the back muscles accentuate the fall. To address this situation the device should be worn on the head, in which case the sequence of logical Conditions would be satisfied and a call placed automatically for help. People who are at risk for this type of fall, might therefore not rely on the default parameter settings, but would have a revised parameter setting so that free fall for the time required for the head to move from the seat of the chair to the floor would reliably be sufficient to satisfy Condition B.

There are a variety of non-purposeful patterns of motion that the arms and wrist can undergo. In yet another scenario the hands of the falling person can perform meaningless action, such as fluttering or vascillation, because the person does not know what to do during the fall and reacts perhaps with pure helpless anxiety. The algorithm uses an approach such as Shewhart's statistical analysis, or the determination of a statistical classifier, to determine whether the wrist motion conforms to purposeful effort. If it determines that the wrist motion is characteristic of purposeful effort, then the determination that a fall has occurred is done on the basis of all three conditions. If it determines that the wrist motion is not characteristic of purposeful effort, then the first condition is eliminated and the determination that a fall has occurred is done on the basis of the remaining two conditions. Note that this part of the algorithm is not necessary for determining that the stereotypical loony (agitated) person who walks around with flailing arms has not fallen, because the condition C would never be satisfied, as the person's arms continue moving and the wrist continues accelerating.

In this part of the algorithm, or optionally in, for example, the part of the algorithm that uses the three conditions but for which the result of the third condition is ambiguous, or optionally if the user is suffering from some form of dementia and the device detects a near fall such as indicated by two of the three conditions being met, then the device optionally sends a signal to the user to ask for a response or to remind the user to take an action. The signal to the user can be optionally a moderated tone or loud claxon leading to affirming or blocking action by the user, a voice message reminding the user to take a positive action such as pushing the button to confirm that s/he needs assistance, or if an automatic call is about to be initiated, a voice message reminding the user to take a positive action such as pushing the button if s/he wants to prevent the automatic call for help.

In one arrangement, the analytical subsystem 34 of the fall detection system 20 has a default value of −0.5 G for parameter β, 72 defining the threshold value for the accelerometer value for condition C, box 64 in FIG. 3, (negative 0.5 G, meaning acceleration in a suddenly substantially reversed direction). As indicated above, the second parameter, β, 72 defines the threshold value for the accelerometer value for condition C, box 64 in FIG. 3, and signifies the stoppage of a fall. Thus condition C evaluates to TRUE if the value for acceleration in region C is a negative value ranging from P to negative infinity, and FALSE if it is greater than β. In one arrangement, as long as condition C is met for the minimum sensing time, the condition is true. There may be situations where the value is in a range that is less negative than β, and a longer time period is needed, such as sliding down the stairs.

Not all falls are necessarily worthy of an immediate emergency call for all people. The value set for β reflects several factors, including a judgment as to the degree of impact that would reasonably yield significant damage to the user. Finally, there is the aftermath of the fall. Although in some cases the body and wrist will come very quickly to a stop after an impact, in other cases, such as during a fall down stairs, the body and wrist will take some seconds to come to a halt. Further, short of motionlessness due to a concussion or worse, one common reaction to a fall is lying or sitting quietly in place for a short time, to check whether one is conscious and physically okay. Thus, during the beginning of this time interval the person is likely to be either moving a great deal but not as a reliable indicator of well-being, or substantially motionless, not as a reliable indicator of either injury or well-being. Thus, there is a period of time T that must elapse before the device begins to evaluate Condition D and Condition E. The period of time τ is adjustable by a qualified person. In one arrangement, the adjustable period of time, τ, which has a default value such as 15 seconds, characterizes the initial recovery time after a fall. If the value of τ is very short, the system will be biased in favor of reporting all physical falls no matter what their impact on the person, that is, favoring false positives, in this case defined as fall events that did not damage the user sufficiently so that s/he was unable to push the manual help button. If the value of τ is very long, the system will be biased in favor of reporting only those fall sequences that have the most severe consequences for the user, such as sustained unconsciousness, that is, favoring false negatives, in this case defined as fall events that damaged the user so severely that s/he was unable to push the manual help button for a long period of time.

An Alzheimers' or other dementia patient would represent an example of a user for whose device the qualified person may elect to set a rather short value of τ, since such a user would not reliably be able to press the manual help button at all. A very healthy person who is still in robust physical and mental condition would be an example of a user for whose device the qualified person may elect to set a rather long value of τ, such as 30 to 60 seconds, since such a user might have falls, but only a sustained period of inaction would be the indicator that a fall merited an automatic call. After the time interval is completed, the person who is not in trouble will have begun to move normally enough, again yielding accelerometer readings in typically small variations around 1 g so that the after-fall condition evaluates as FALSE. If after this time τ, the inventive device indicates that the person continues not to move, or if there are strong negative or positive accelerations that would characterize such conditions as writhing, which conditions can be detected as out-of-normal motion sequences through statistical analysis such as discussed earlier, then the after-fall condition evaluates to TRUE.

Figure 6:
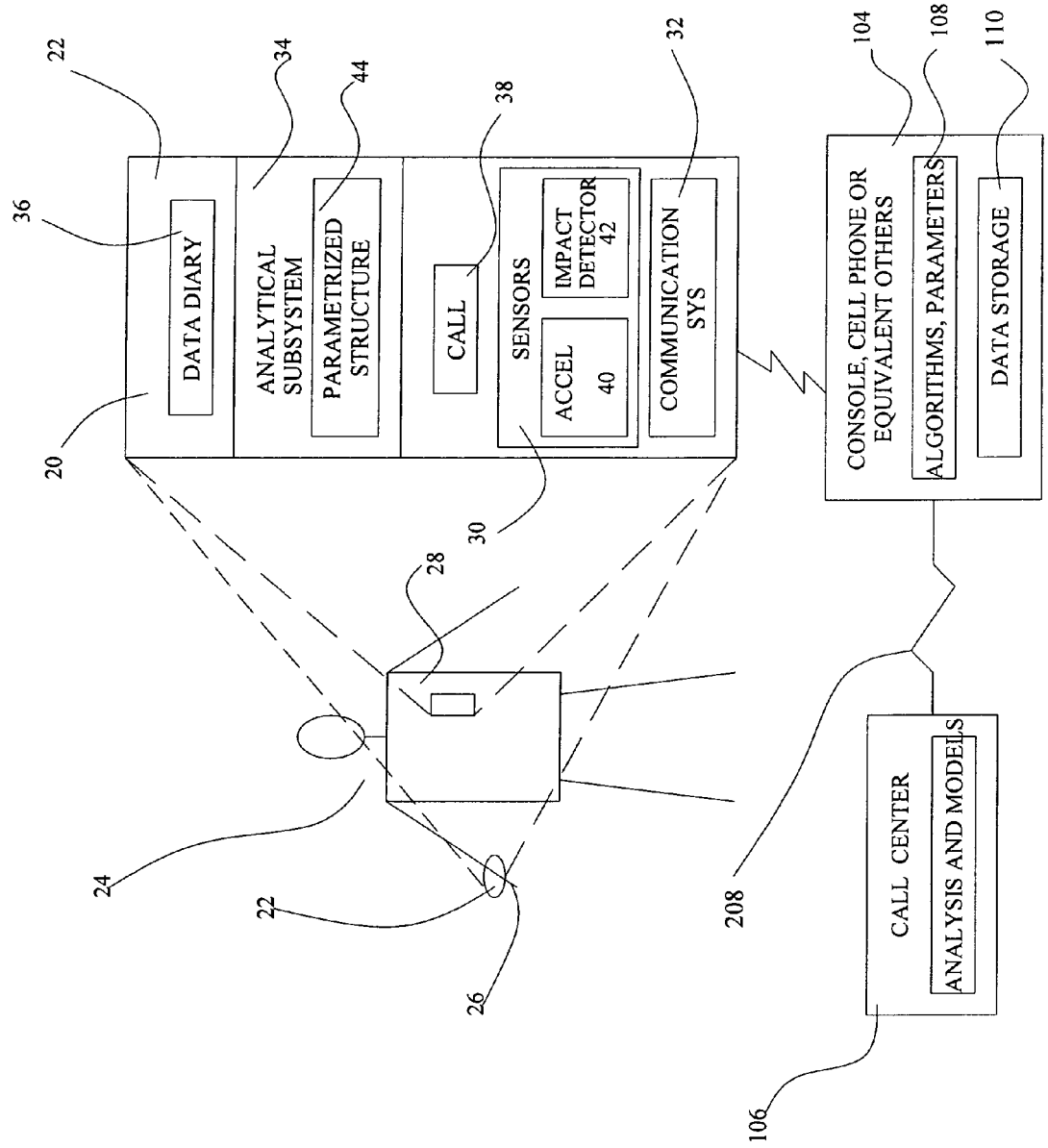
FIG. 6 is a block diagram of a motion analysis tele-monitoring system.

Referring to FIG. 6, the wearable fall detection monitor device 22 of the fall detection system 20 is shown in a block diagram with a console 104 and a call center 106 of the system 20. The wearable fall detection monitor device 22 of the fall detection system 20 is configured to be worn by a person 24 on such locations as the torso, the wrist, the head, and the belt. The wearable fall detection monitor device 22 communicates with the console 104. The console 104 is typically located somewhere physically proximate to the wearable fall detection monitor device 22 of the fall detection system 20. The console 104 communicates with the call center 106 that provides administration for the system 20 and passes alerts to caregivers. In an alternative embodiment, the console 104 is programmed with the telephone number of a triage center which may be provided by the user, or by any third party.

The wearable fall detection monitor device 22 of the fall detection system 20 includes the communication system or interface 32, the sensor system 30 having at least one sensor 40, the analytical subsystem 34 with at least one parametrized structure 44, and the data storage system 36. In one arrangement, the wearable fall detection monitor device 22 includes the call button 38 to be used by the wearer of the wearable fall detection monitor device 22 to call for immediate help. This button may preferably include an alternative option, such as a multiple button click or a separate button, to truncate an emergency call or to indicate to the call center that the user is OK even though an automatic call has been made.

Still referring to FIG. 6, the wearable fall detection monitor device 22 in an arrangement is a low-power proactive tele-monitoring system in which the sensor system 30 includes an accelerometer 40. (The fall detection system 20 is sometimes referred to as the tele-monitoring system). The analytical subsystem 34 takes as input the data from the accelerometer 40. The analysis performed by the analytical subsystem 34 on the accelerometer data may optionally include impact detection with an impact detector 42.

The communications system 32 is preferably a short-range (approximately 10 to 200 m) digital radio system. The wearable fall detection monitor device 22 continuously monitors and parses the data stream of the accelerometer. This is supported by a FIFO (First In First Out) buffer in memory to retain the most recent data prior to the onset of a fall event and the data about the details of the fall and its immediate aftermath, to be stored in the diary in the event of a fall or near fall and subsequently transmitted to a location such as the call center. When the event is over, or during a convenient later time, the contents of the FIFO buffer are written to the data storage system 36, after which the buffer is written over through the process of normal operations. The data storage system 36 enables a person to be monitored for incidents of fall-related behavior over a period of time.

Based on this data and other factors, parameters such as the threshold levels a and β and time of condition such as condition A, condition C, and condition D can be adjusted to minimize false positive and false negative results. In an arrangement, the system is set so that only qualified persons who can set and adjust the parameters of the system can obtain feedback about the quality of their settings for the user, and then modify their settings to provide an improved fit to the user's needs and situation. At times of convenience or upon command, the wearable fall detection monitor device 22 transfers the contents of the data storage system 36 through the console, through a cell phone, or by transferring a manual storage device such as portable flash memory or small non-volatile memory mini-SD media to a server, or by wireless radio to a console for further processing or forwarding depending on the configuration of the system. The period of monitoring and storing depends on the capacity of the mini-SD media as well as operational considerations.

Still referring to FIG. 6, while the wearable fall detection monitor device 22 of the fall detection system 20 communicates with the console 104 wirelessly in this embodiment, it is recognized that other types of communications links are possible. For example, in one alternative arrangement the wearable fall detection monitor device 22 is connected to a receiving device connected to the console 104 over a local area network. In one arrangement, the receiving device does not contain any circuitry to process data, although in other embodiments it may. It deals with data on the basis of store and forward to reduce the risk that data may be lost. It is the primary repository of retained data about falls, making it possible for the worn fall monitor to have minimal non-volatile storage and therefore remain lighter and smaller. It is able to attempt multiple calls through multiple channels to the call center or other designated loci, in case one or more of the communications channels has broken down. There can be receiving devices in multiple rooms all connected to the console 104, or multiple consoles in separate parts of an occupied space, all coordinated so that only one console will place a call to the call center even if more than one console receives a fall alert from the worn device.

In another alternative arrangement, the wearable fall detection monitor device 22 is connected to the console 104 directly in order to transfer data from the data storage system 36 to the console 104. The communication system 32 has two methods of transferring information. The first method is wireless for indicating when a fall occurs. The second method is when the fall detection monitor device 22 is docked into the console 104 for transmitting larger amounts of stored data.

In another arrangement, the communication system 32 of the wearable fall detection monitor device 22 is similar to a cellular telephone system and is able to transmit data to the console 104 or a call center from a remote location. In one arrangement, the console 104 is an application included in a cellular telephone carried by the wearer of the wearable fall detection monitor device 22.

In one arrangement, the part of the device that constitutes the wearable fall detection monitor device 22 and the part of the device that communicates with the console 104 are separate, in which case more than one of the parts that constitute the wearable fall detection monitor may communicate with the worn part of the device that communicates with the console, and that resulting aggregation and communication device may be called a hub, which may be located anywhere on the body, although it would typically be located somewhere on the torso where it would be roughly equidistant from sensors located anywhere on the body, and where it could have extra battery weight that would be easily borne by the user. In the combined wearable fall detection monitor device 22 and console 104, the system may include a wide area network (WAN) interface and may also be able to communicate directly to the call center 106. Some of these configurations enable the wearer of the wearable fall detection monitor device 22 to be monitored at a greater distance from the console 104.

Still referring to FIG. 6, the console 104 also includes an analytics subsystem 108 including at least one parametrized structure and a data storage subsystem 110. The console 104 is typically physically proximate to the wearable fall detection monitor device 22 such as in the same building, a house or apartment, for example. The console 104 receives alerts from the wearable fall detection monitor device 22 and relays the received data to the call center 106 through a wireless connection, a local-area or long-range communications network. In addition, the console 104 provides some amount of local storage in the data storage subsystem 110 in part to foster fault tolerance. The data storage subsystem 110 enables the console 104 to re-send information to ensure the reliable notification of caregivers. It also enables retrieval and transfer of detailed data about falls and near falls to permanent storage. The console 104 also includes an internal electronic clock so that information can be time-stamped and routine communications scheduled for the most suitable hours of the day or night.

Where the console 104 is a home-based monitoring console, the console 104 is preferably located so that radio coverage is provided for the entire dwelling area. If a single console 104 cannot provide sufficient coverage for the entire occupied area (because the dwelling is very large, because of localized interference, or because separate buildings or outdoor spaces are also to be covered), additional consoles may be employed to extend the coverage area. In those embodiments in which more than one console is used, each console 104 has its own telephone connection (or other communications connection). Separate telephone numbers or extensions for multiple telephone-based consoles are optional and usually not necessary.

In the event of a fall or a call button press, the wearable fall detection monitor device 22 immediately contacts the console or cell phone ("console") 104, which in turn relays a distress alert to the call center 106. The console accordingly also gives calls to caregivers as appropriate, or alternatively the call center 106 in turn contacts caregivers.

In the event of an emergency, the console 104 initiates the connection to relay the information to the caregiver. The console 104 in this embodiment continues to attempt the communication until the communication has been completed successfully such as determined by an acknowledgement to the console from the call center 106.

It is recognized that the above describes one arrangement. There can be other arrangements such as in which the console 104 communicates with the call center 106 (alternatively, with designated caregivers) indirectly, either through a communications connection such as the telephone system to the Internet or some other network. In this arrangement, the console 104 communicates with a third party (such as an automated call center) whose task it is to then relay and present the information to the call center 106 (alternatively, with caregivers) as appropriate.

Several embodiments of the console 104 are possible depending on the specific needs of the user installation. For home-based monitoring, an example console 104 takes the form of a desktop box that is centrally located in the house and is connected to telephone lines. The use of other long distance communications networks, such as cellular telephone networks, 3G and 4G cellular telephone networks, WiMAX, DSL, cable modem, and other wired and wireless "backhaul" networks are also foreseen by this invention. In this embodiment, the console 104 contains a radio receiver, a telephone (or other "backhaul" communications) interface, a wall-power system with battery backup, and enough storage and processing power to perform the required console functions. In addition, the console 104 itself may provide an emergency call button or "hot key sequence" to complement the call button on the wearable fall detection monitor 22.

Figure 7:
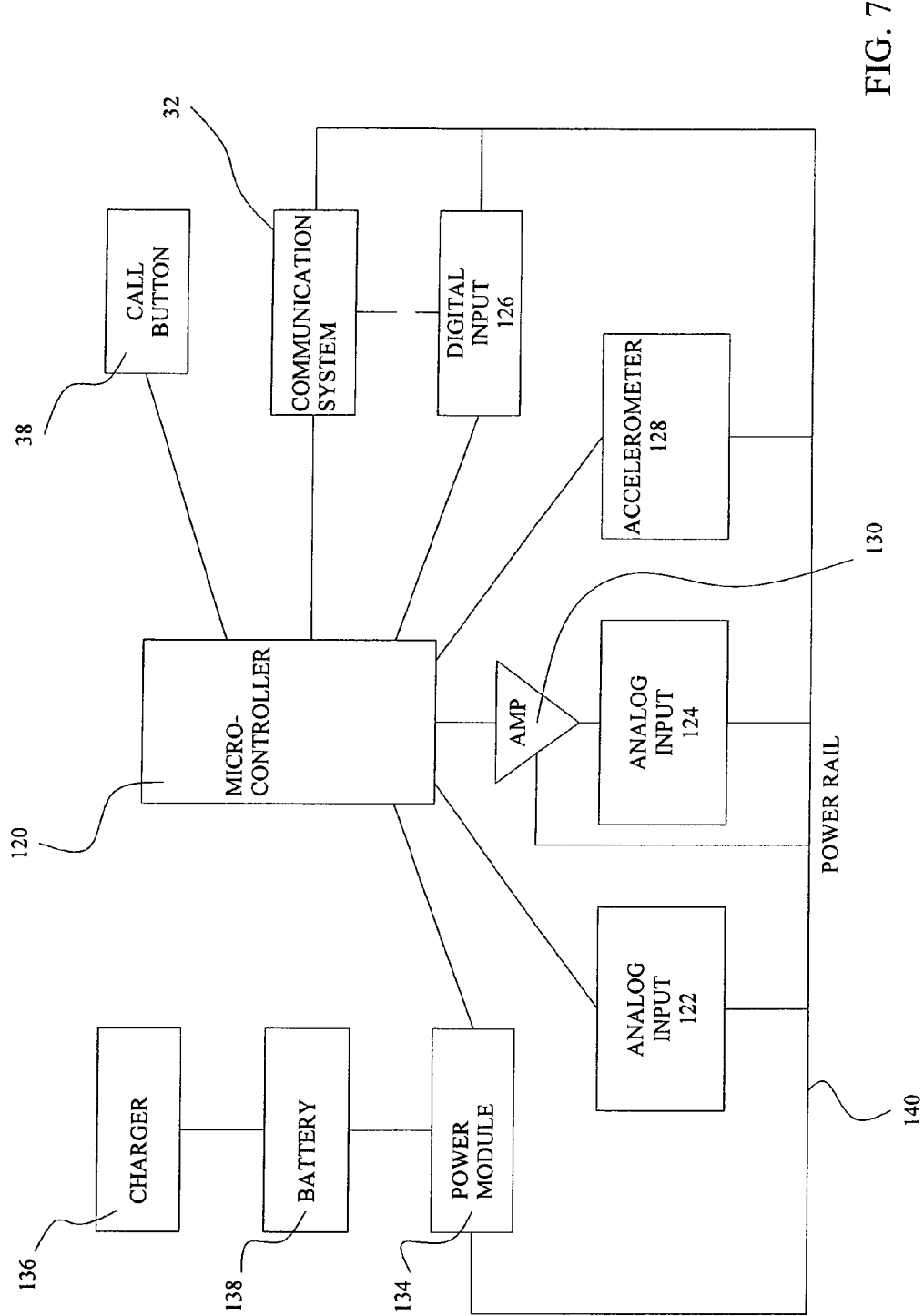
FIG. 7 is a schematic diagram of the device.

Referring to FIG. 7, a schematic of the components of the fall monitor device 22. The wearable fall detection monitor device 22 of the fall detection system 20 has a microcontroller 120 connected to a plurality of devices including at least one unbuffered analog input 122, at least one buffered analog input 124, at least one digital input/output 126, and an accelerometer 128.

The microcontroller 120, the central component of the fall monitor device 22, is illustrated. The microcontroller 120 has sufficient main memory to support the software algorithm and data management that are central to the identification of falls, as well as optionally sufficient volatile or non-volatile memory to support storage of data on a small number of fall candidates, with non-volatile storage as another alternative for a data diary stored for longer periods of time.

The algorithm which is symbolically shown in FIG. 4 is stored in the program register of the microcontroller 120. The parameters that determine if the various conditions (e.g., condition B, condition C, etc) are met, including the threshold parameters of $\alpha$ and $\beta$, and time, can be adjusted by a person based on fundamental knowledge of the wearer or the wearer's class, or based on data stored either in the microcontroller 120 or that has been transmitted to the console 104.

The buffered analog input 124 is buffered by an amplifier 130. The buffered analog input 124 has a ground referenced DC amplifier to be compared to the output of the accelerometer 128. The accelerometer 128 is preferably a 3-axis accelerometer to allow for the detection regardless of the orientation of the wearable fall detection monitor device 22. In addition to the accelerometer 128, there is optionally an impact detector 132 such as developed by Natick Laboratories.

The microcontroller 120 examines the input from all three axes of the accelerometer. The microcontroller 120 determines in what direction there is a G force; the direction may not and likely will not correlate with one of the 3 axes of the accelerometer. The microcontroller 120 through the algorithm determines the magnitude and direction of the force that would produce acceleration. As has been discussed above, the absolute orientation of this direction does not matter. What matters is the magnitude of the G-force and the direction in each sample, as well as in relation to other samples. In other words, during the first stage of a fall, the magnitude of the accelerometer reading drops to significantly less than 1 G. During impact the movement changes direction substantially in the reverse direction as a result of G forces of high magnitude. During the third stage of the fall what matters is not the direction of motion and the G-force measured by the accelerometer of itself, but rather the magnitude and direction of the G-force characterizing that impulse or change in motion that is measured and understood in relation to the motionlessness that results in the fourth stage of the fall.

In addition to algorithmic differences in the above, the only major physical differences of the wearable fall detection monitor device 22 dependent on the location it is placed, for example the wrist 26 or the chest 28 are the attachment means and the size, weight, and location of the buttons and antenna for communication. The analytical subsystem 34 of the wearable fall detection monitor device 22 has different threshold parameters to account for the difference in location. It also must give consideration as is described herein to extraneous motions that are possible with the arms and wrists.

A power module 134 conditions and provides power to the components. In addition to the power module 134, the wearable fall detection monitor device 22 has a charger 136 for the charging of at least one battery 138. Optionally, replaceable batteries are used. The battery 138 provides power to the components of the fall detection monitor 22, unless the fall detection monitor 22 is docked such as in a console 104 to charge, or unless replaceable batteries are used. The power, regardless if it is from the docking or battery, is conditioned by the power module 134 and forwarded to various components by a power rail 140.

In addition, the wearable fall detection monitor device 22 of the fall detection system 20 has the communication system 32 and the call button 38 connected to the 1 5 microcontroller 120. In one arrangement, the threshold parameters, including $\alpha$ and $\beta$ are adjusted by transmitting information from the console 104 wirelessly or through the docking station such as in a console 104 to the wearable fall detection monitor device 22; the data is fed from the communication system 32 to the microcontroller 120 through the digital inputs 126.

Figure 8:
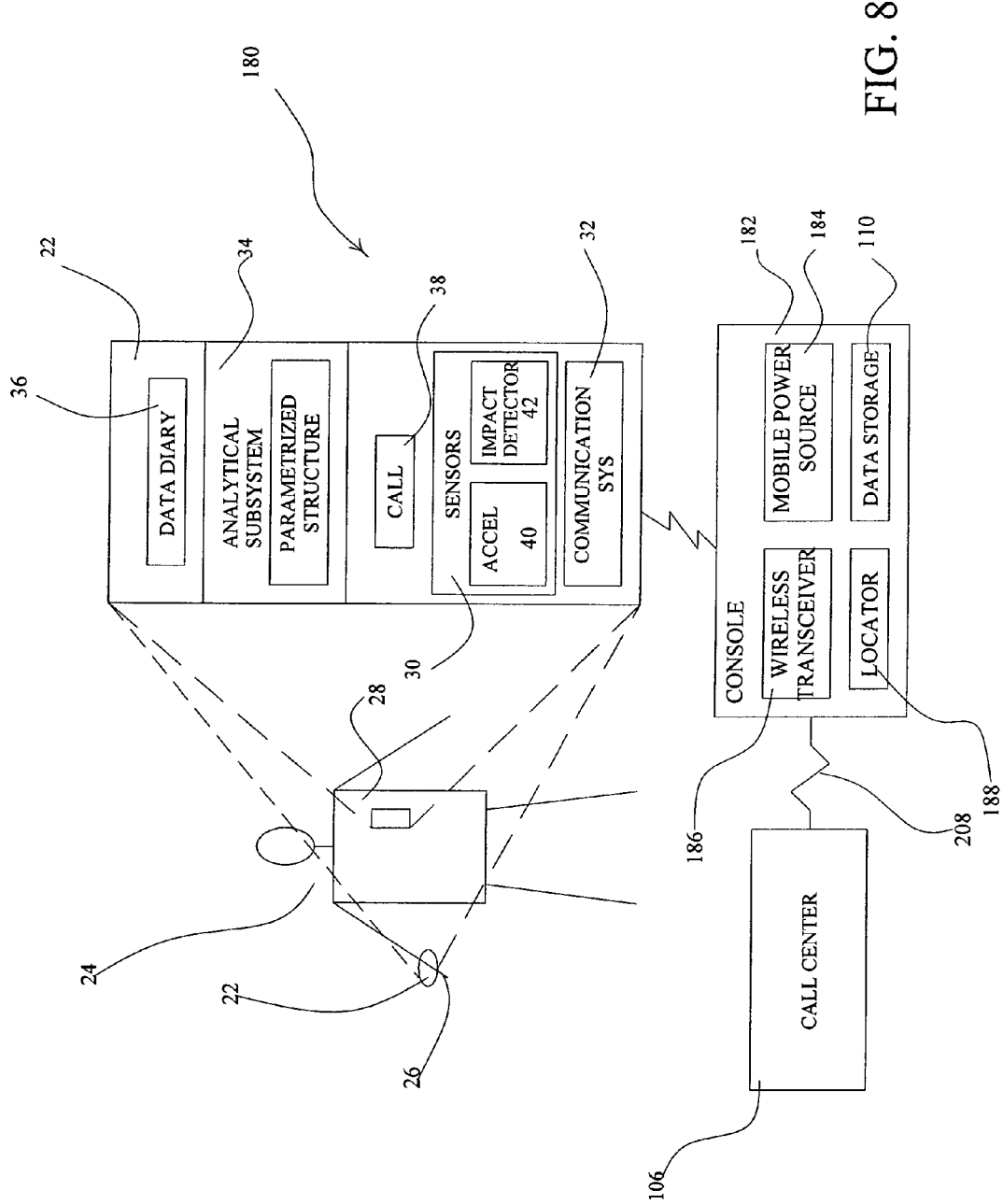
FIG. 8 is a block diagram of a mobile motion analysis tele-monitoring system.

Referring to FIG. 8, a mobile tele-monitoring system 180 is shown. The mobile tele-monitoring system 180, a fall detection system, includes a wearable fall detection monitor device 22 worn by the person 24 being monitored. The mobile tele-monitoring system 180 further includes a mobile console 182. The mobile console 182 enables monitoring for those people who require monitoring outside the home (or other fixed location). The mobile console 182 includes data storage 110. The mobile console 182 further includes a mobile power source 184 making the console 182 portable. The mobile power source 184 is, for example, a rechargeable lithium polymer battery based power regulator circuit. The mobile console 182 also includes a wireless communications system such as a wireless transceiver 186. For example, one arrangement of the mobile console 182 combines a radio receiver to receive transmissions from the wearable fall detection monitor device 22 with a "cellular telephone" (GSM, GPRS, CDMA/TDMA, etc.) radio module.

In one arrangement, the wearer 24 of the wearable fall detection monitor device 22 carries (or wears) the mobile console 182 in addition to the wearable fall detection monitor device 22. In another arrangement, the mobile console 182 is located nearby such as in a vehicle. In either case, the wearable fall detection monitor device 22 monitors the person 24 as described above and records the fall data in the data storage system 36 or the Call Center. The data storage system 36 is periodically transmitted to the mobile console 182. The wearable fall detection monitor device 22 also detects a fall, for example, or call button activation and transmits a distress message to the mobile console 182.

Unlike a location-based system, the mobile monitoring system 180 optionally includes a locator 188 in the console 182 in order to report the location where aid is needed. In a first arrangement, the locator 188 is a global positioning system (GPS) device enabling the console 182 to transmit the location to the call center 106. In a second arrangement, the locator 188 makes a cellular telephone connection and the console 182 can be found through known triangulation techniques. In a third arrangement the worn hub is a cell phone with a GPS, so that the coordinates can be read from the cell phone and transmitted. Alternatively, a locator 188 is included in a wearable fall detection monitor device 190 as shown in the embodiment described below with regard to FIG. 9.

Figure 9:
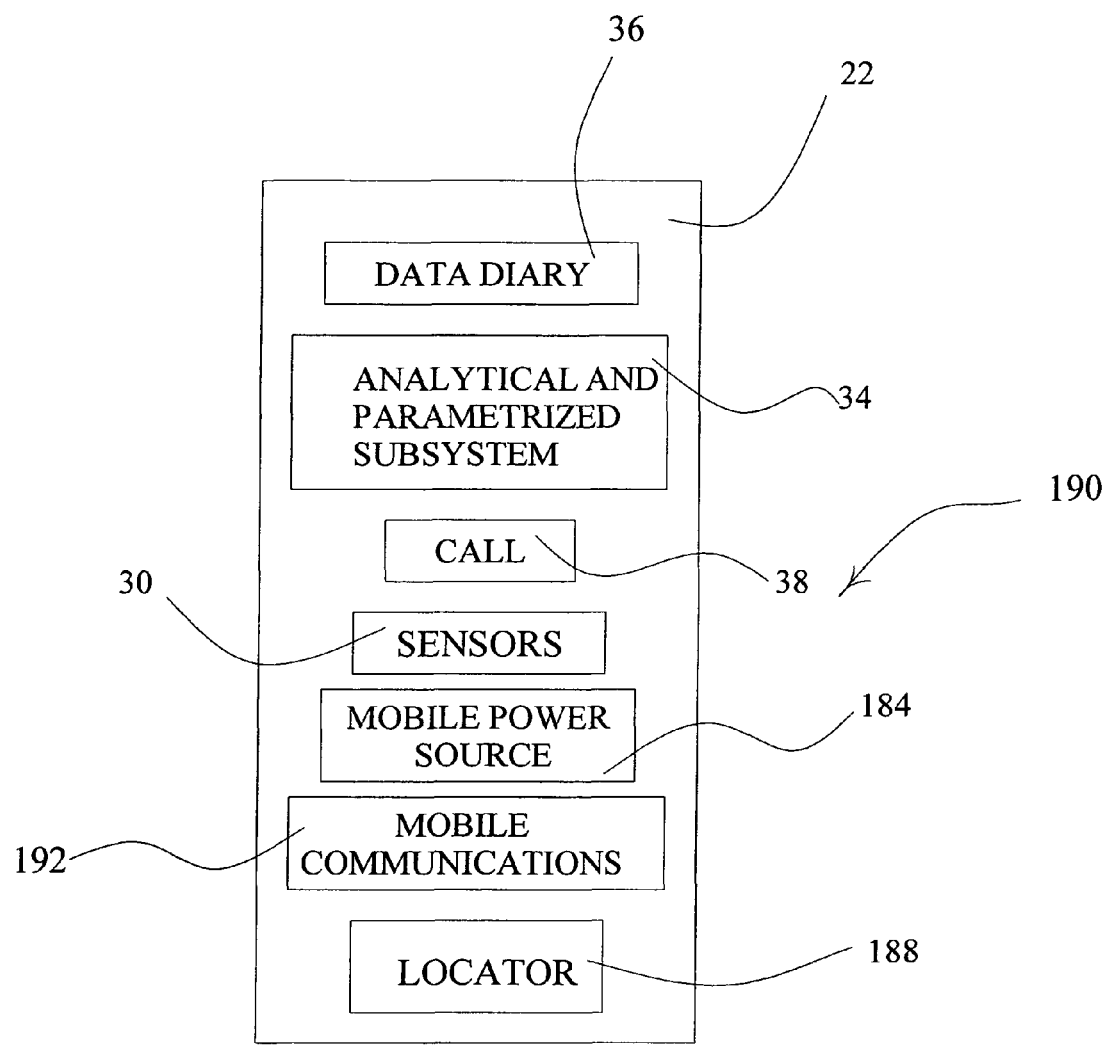
FIG. 9 is a block diagram of a mobile monitoring device.

FIG. 9 shows an alternative arrangement of a wearable fall detection monitor device 190 enabling monitoring away from a fixed location. The wearable fall detection monitor device 190 includes at least one sensor 30 to monitor the person wearing the wearable fall detection monitor device 190. The wearable fall detection monitor device 190 further includes algorithms 34 for analyzing the collected sensor data. The wearable fall detection monitor device 190 also includes a data storage system 36 to store data and a call button 38 as described in previous arrangements. The wearable fall detection monitor 190 further includes a mobile communication system 192 to transmit data to a fixed-location console or directly to a call center. The mobile communication system 192 interfaces for example with the wearable fall monitor wearer's cellular telephone to communicate with a console or a call center. The wearable fall detection monitor 190 further includes a mobile power source 184 that powers the wearable fall detection monitor 190 in order to perform monitoring operations and to communicate with a console or call center. In one arrangement, the wearable fall detection monitor 190 is locatable using the cellular telephone connection using known techniques such as triangulation. In a second arrangement, the wearable fall detection monitor 190 has a locator 188 which is, for example, a GPS device.

In another arrangement, a tele-monitoring system combines the mobile console 182 with one or more fixed-location monitoring consoles 104 (e.g., home-based consoles) to provide comprehensive monitoring.

Figure 10:
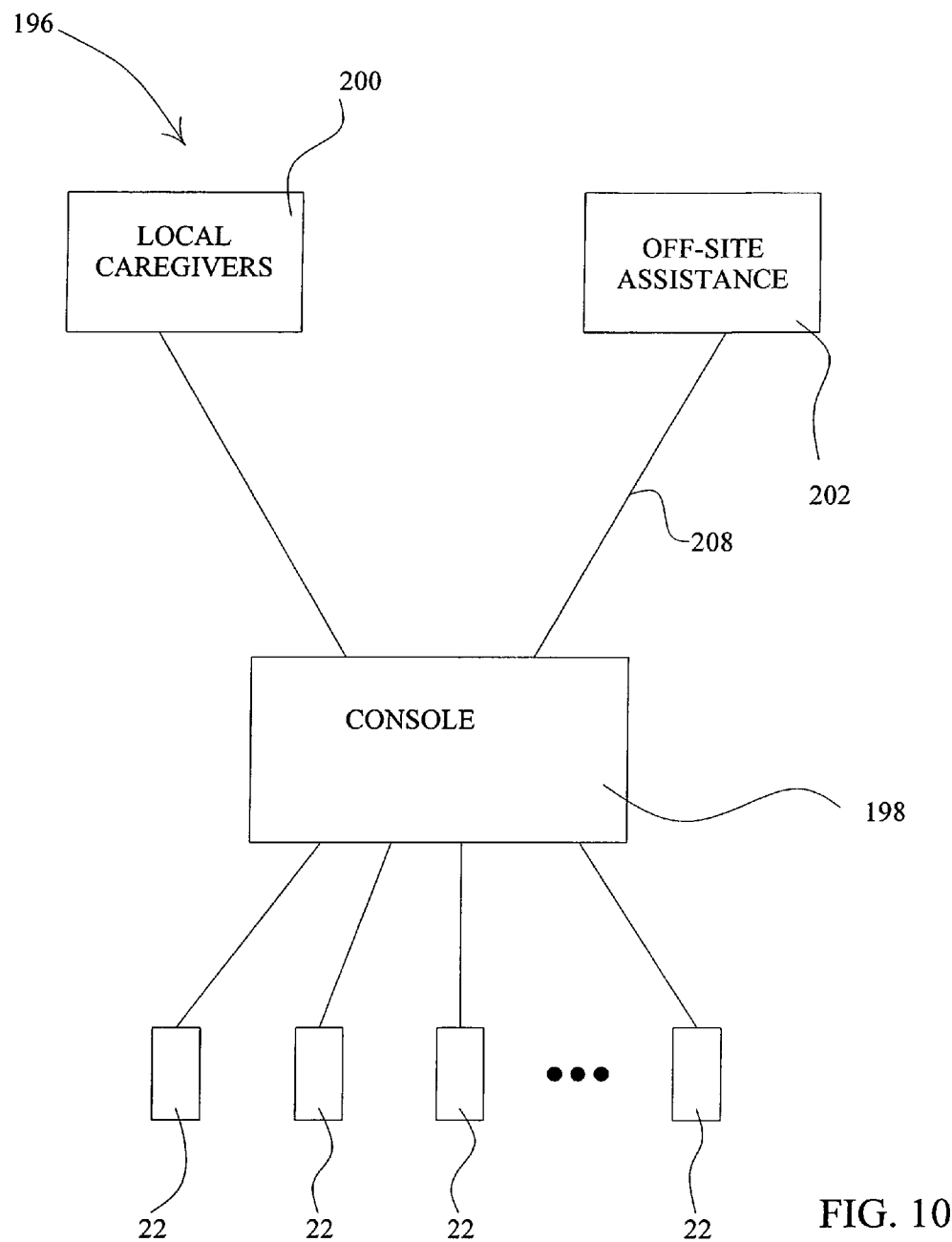
FIG. 10 is a block diagram of a tele-monitoring system having a plurality of wearable monitoring devices in communication with one console.

Referring to FIG. 10, a schematic view of a tele-monitoring system 196 having a plurality of wearable fall detection monitors 22 communicating with a console 198 is shown. This system 196 is useful in an institutional setting such as an assisted care facility. Further, in an institutional setting, the console 198 often communicates directly with a local caregiver 200 rather than communicating with an off-site call center 202. The link between the console 198 and the local caregiver(s) 200 is for example a wireless or a wired local area network. In an alternative arrangement, the console 198 is configured to communicate directly with a designated call center 202, with off-site emergency personnel, such as making a 911 connection or by calling a local fire department or police department. In some arrangements of the console 198, the console 198 receives messages from smoke, fire, RFID, or other detectors installed in the building as well as messages from wearable fall detection monitors 22. A wide range of emergency response options is possible ranging from the notification of in-house responders to direct dial of police, fire, or 911.

The factors that distinguish institutional deployment from residential use include that there is a greater likelihood that there will be a larger number of wearable fall detection monitors 22 than consoles 198 in an institution, and the likelihood that at times there will be a large number of monitors 22 in the proximity of a single console 198 in an institution. A single console 198 with a plurality of wearable fall detection monitors 22 may also be used in some residential co-housing situations that are not strictly speaking "institutional" such as both members of an older couple using wearable fall detection monitors 22 in a home with a single console 198, or a multiple of families using a console in a common area. Additionally, in an institution, there is often a presence of an in-house emergency response service, which is not typically present for most non-institutional facilities.

Where there are a plurality of consoles 198, one console 198 is designated a main console for the purposes of transmitting alerts. The use of a main console avoids the possibility of confusion if multiple consoles were to issue alert signals based on a single event. Redundancy schemes are included in the console network to ensure that alert notifications are carried out. In one arrangement, the consoles 198 generate an alert to emergency responders automatically upon receiving a signal from a wearable fall detection monitor 22. In a second arrangement, a monitoring person moderates the alert signals by verifying that an emergency situation exists prior to forwarding the alert to emergency responders. Regardless of the arrangement, the fall detection system 20 determines that a fall has occurred based on the analytical subsystem 34 of the fall detection monitor 22 determining that the data meets the required conditions; the monitoring person is not required to analyze the raw data to initially determine if a fall has occurred. At the same time, because the raw data can be made available to the monitoring person, the device can be set so that it alerts the monitoring person to a likely fall, and then allows the monitoring person to view that data in order to make a decision about what action, if any, to take.

The fall detection system 20 of FIGS. 6 and 8, the mobile tele-monitor system 180 of FIG. 9, and the tele-monitoring system 190 of FIG. 10 include a reliability system to confirm communication has gone through. A method and system is implemented in the communication links 208 between the consoles 104, 182, and 198 and the call center, Call Center 106, as well as between consoles in a plural console network. For example, message acknowledgments can be implemented in links 208 with bidirectional communications, particularly where the communications are of low-latency. Data transfer by modem (from console to call center), for example, is easily made reliable because the circuit-based full-duplex communications channel allows rapid acknowledgement. A notification delivered by pager or telephone short message service (SMS) is more difficult to make reliable because it is difficult to guarantee that the message will actually be seen by the recipient even when the message is successfully delivered to the receiving device. In some circumstances, it will be possible to require that such notifications be acknowledged by an action taken by the recipient such as requiring a caregiver to send a reply message to a telephone SMS message, but there is substantial risk that these additional actions are unreliable. For example, one may not remember to acknowledge a telephone message if one is rushing off to check on someone who has fallen and may be severely injured.

Redundancy strategies can be included in arrangements in order to ensure that an alert message is transmitted to a responder. For example, in one arrangement, the console notifies the first caregiver on the list and if a positive acknowledgement is not received the second one is contacted, etc. Another arrangement relies on a call center that supports a range of notification options, from telephone calls to pages to SMS messages.

One of the key issues for a device that operates only occasionally is reasonable verification that it is still functioning properly so that there is a reasonable expectation that it will perform when called upon to do so. Conventional manual call button services lack the periodic reporting feature of the fall monitor system, and thus failures may go undetected for as long as the system remains untested. One way to do this verification is to trigger trial alarms. A representative of the call center can contact the user, who can push the button to trigger an alarm, and the caller can verify that the alert came through to the call center. However, there is also a need to verify the automatic alarm capability to the extent possible.

One way is for the caller to arrange for the user to drop the device to the ground and wait for the alert to come in verification to the call center. This, however, places a burden on the user, who may not be capable of performing this function. It is desirable to have a method for verifying functionality that is independent of the user. The automated internal check of selected functioning of the system and its components is controlled in software running on the microcontroller and is either triggered by an external command or performed on an automatic scheduled basis periodically, such as once every week. The algorithm checks each component of the wearable fall detection monitor 22 to verify that it is functioning according to the verification conditions, and sends as little as a single bit of information to the console for pass through to the call center to indicate that everything is functioning properly, or not. This check for example runs through the internal checks provided with the accelerometer and the microcontroller, then reports to a separate line in the call center that the test was successful or not. Certain parts of the device are implicitly checked by this process and may not require separate automated verifications. For example, the fact that a command was received and in turn triggered the check provides evidence that the digital input channel is functioning properly. The fact that the device successfully radioed the results provides evidence that the radio system is working properly. Time stamping the transmitted information provides indication that the system clock is functioning properly, as well as providing part of a unique identifier for the information. To minimize use of power and valuable time on the communication channels, minimal bits of information need be transmitted to indicate a successful check. The connection for these periodic or on-command checks can also serve for transmission of any fall data that may have been stored by any worn fall monitor, hub, or the console. Those skilled in the art will recognize that additional information can be sent in additional bits with minimal impact on the longevity of the battery life or the time to transmit and read this information at the console or at the call center.

In addition to the console, 104, 182, and 198 contacting the Call Center 106 or off-site assistance center 202, remote caregivers or technicians at a Call Center can initiate the connection with the console 104, 182, and 198. This "pull" communications arrangement is desirable under some circumstances such as verifying that equipment is working, performing remote maintenance, or maintaining a working relationship with users. In addition, the parameters such as the threshold levels β, α, and τ can be adjusted using this "pull" communication.

Figure 11:
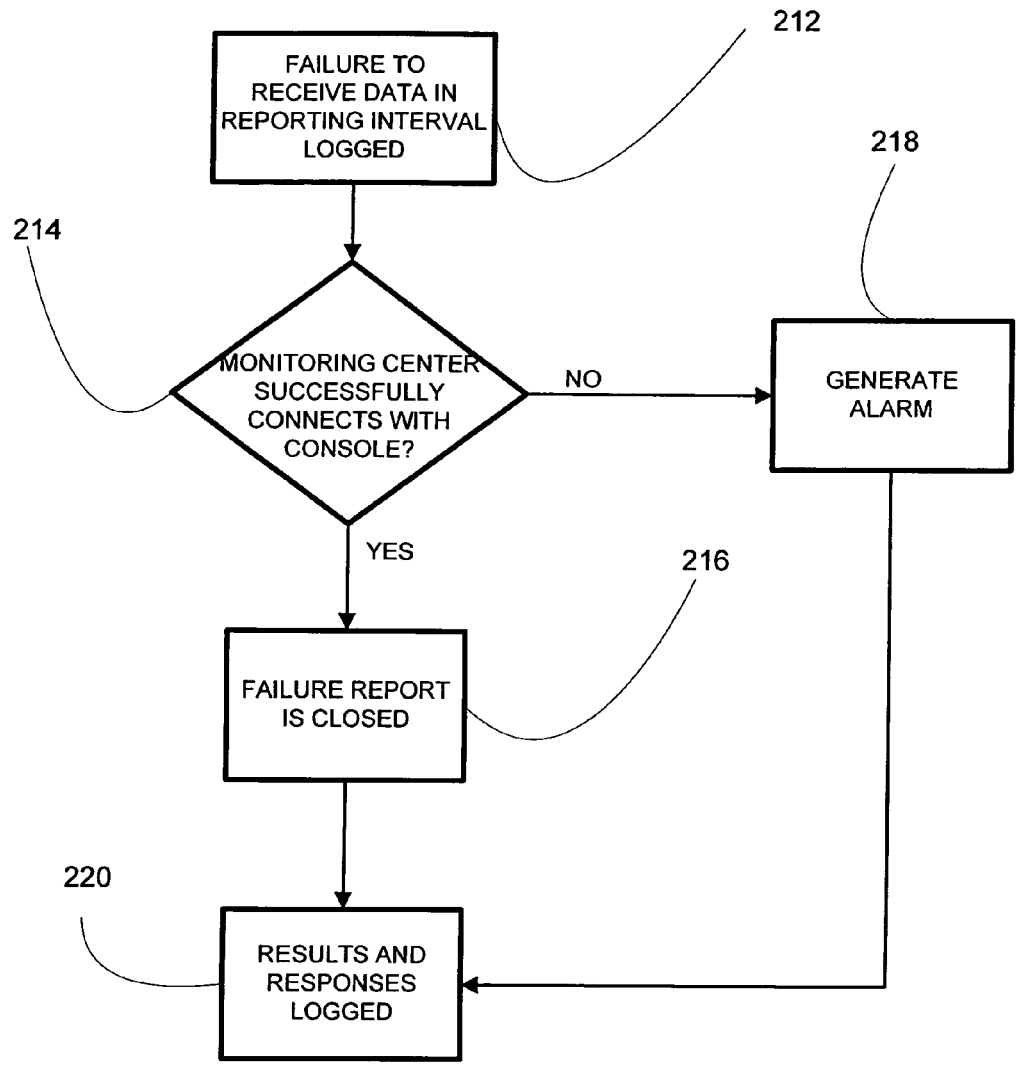
FIG. 11 is a flow chart of error handling in a tele-monitoring system having a central monitor.

Referring to FIG. 11, a flow chart of the operation to handle a communications failure between the console 104 and the Call Center 106 is shown. A communications failure between the console 104 and the central Call Center 106 is handled differently than a communications failure between a wearable fall detection monitor 22 and the console 104.

A failure to receive data from a console 104 within some predefined reporting interval results in a logging of the failure at the Call Center 106 as represented by block 212. The predefined reporting interval is a settable interval. The interval in one arrangement is, for example 7 days. Thus the console 104 automatically sends some message or information to the Call Center 106 during a set time range in each such call interval. If the user is off to another location and the console 104 has been properly set such that the console 104 is not noting a failure of the wearable fall detection monitor 22, the message will be that there is no message or information that has to be sent by the console 104 to the Call Center 106.

It is recognized that the type of signal the console 104 sends the Call Center 106 can differ depending on the situation, such as the person is present but in trouble without having fallen. Thus, differing signals can be sent by the fall monitor depending on such conditions. In one embodiment there is no emergency message sent but a message indicating presence and/or activity if the accelerometer trace indicates some sort of activity by its variation over the period. If there is a fall then there is an emergency message sent, then both the console 104 and Call Center 106 know that the wearable fall detection monitor 22 is in proximity. If there is no fall and no activity, the wearable fall detection monitor 22 sends the default null signal so that the console 104 and thus also the Call Center 106 know that the fall monitor is functioning and in proximity. If the wearable fall detection monitor 22 is not in proximity, then the console receives no signal at all, and it can notify the Call Center 106 accordingly.

If the Call Center 106 does not receive a report from the console 104, it 106 attempts to establish a connection to the console 104 which in turns reports that the wearable fall monitor checks out, after the failure to receive data is perceived, as represented by block 214. If the Call Center 106 is successful in contacting the console 104, the failure report is closed and further failure response is abandoned as represented by block 216.

In one arrangement, the Call Center 106 does not close out the failure report until the Call Center 106, typically a person, communicates with a person at the monitored site to verify that there is no medical (or other) emergency and that the wearable fall monitor 22 and console 104 are functioning properly. After this validation is completed, and appropriate action taken, the failure report is closed out.

In another arrangement, a computerized inquiry program is implemented. A computer inquiry is transmitted to the console site. The inquiry, is for example, out-of-band such as over a telephone line other than the telephone line connected to the console 104. A person at the console site responds to the inquiry by either providing a voice response if the Call Center 106 has a person or a voice recognition system, or by transmitting a response through the console 104 itself. The Call Center 106 closes the failure report upon receiving a response that the person is well and the wearable fall detection monitor 22 and console 104 have been repaired or are operating properly.

If the Call Center 106 cannot contact the console 104, an alarm is raised indicating that the console is not responding, as represented by block 218. Depending on the circumstances and preferences of the caregivers, this could be a "first class" alarm that results in immediate notification, or a "second class" alarm (other examples might include "low battery") that notifies the caregiver in a less urgent way—by sending e-mail or calling during business hours, for example.

The failure or success results are logged as are any actions such as validations or alarms sent, as represented by block 220.

A console 104 communications failure with a centralized Call Center 106 is also, for example, discovered by a caregiver attempting to contact the console 104 for a routine report. At that point, the caregiver is relied upon to respond to the situation. This is typically treated as a serious problem, since such a communications breakdown could prevent the delivery of urgent notifications.

With details of the fall detection system 20, a higher level discussion follows. The fall detection system 20 is not triggered by changes in body orientation. Instead, the fall detection system 20 responds to a sequence of algorithmically determined events that indicate that a seemingly damaging fall has occurred. The standard thresholds are reviewable and customizable by qualified personnel to tailor the system to the user based on several factors including data that is stored in the data storage system 36 of the wearable device 22 and the data storage system 110 of the console 104. As a result of the sequence of algorithms for determining if a fall has occurred, the wearable fall detection monitor 22 can be worn while lying down, sleeping, reclining, or engaging in a full range of daily activities without risk of unreasonable numbers of false alarms.

Figure 12:
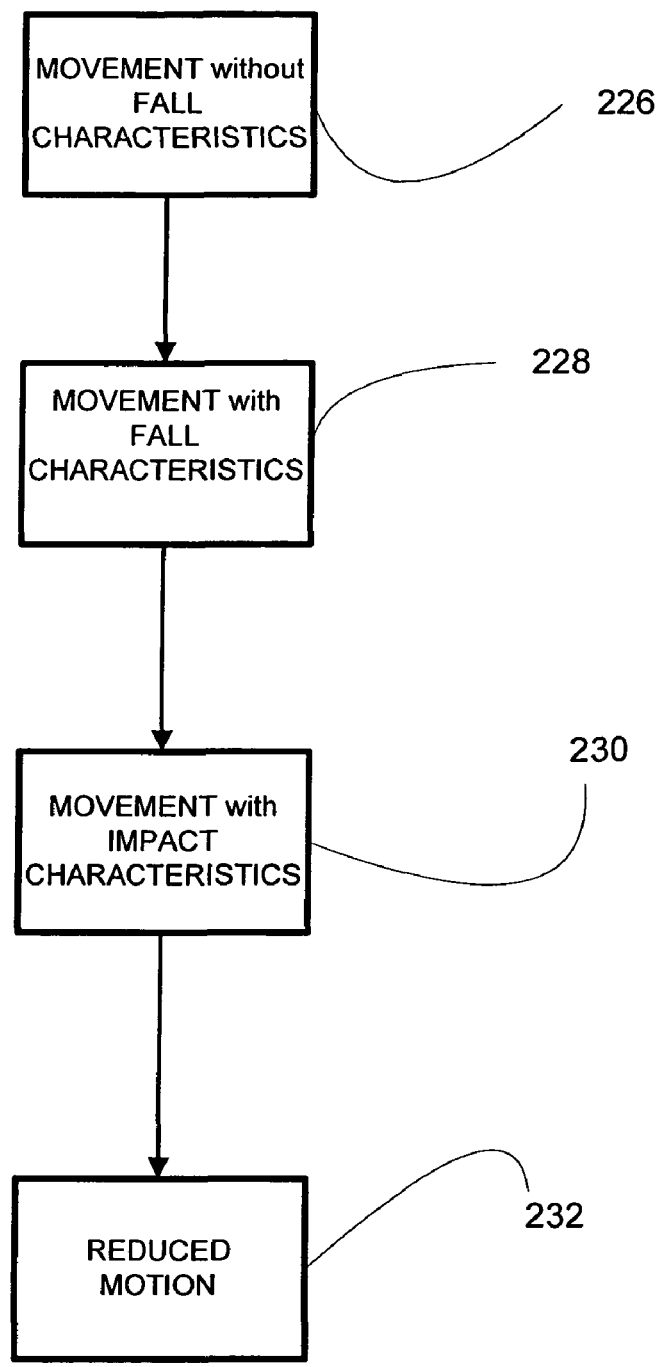
FIG. 12 is a block diagram illustrating the progression of movements in the motion signature associated with a fall.

Referring to FIG. 12, a block diagram illustrates the progression of movements that are typical of a fall, i.e., the "event sequence" of a fall. The user wearing the wearable fall detection monitor 22 is moving about normally, as represented by block 226. The sensor(s) 30, as seen in FIG. 6, such as the accelerometer 40, associated with the wearable fall detection monitor 22 detects movement that the analytics of the system 34 compute as non-fall activity. This need not be a sophisticated determination. It suffices for the present device that the accelerometer 40 track has small variation around the value of 1 G.

The user exhibits movement which the wearable fall detection monitor 22 determines to be characteristic of a fall, as represented by block 228. The details of this fall may vary from a free fall, as if the person's legs disappeared and s/he fell unobstructed to a surface, to a toppling fall in which the person gradually falls and perhaps bumps up against a vertical surface and then slides down that surface, to a complex fall which occurs in a sequence of stages, each with different acceleration. The accelerometer 40 associated with the wearable fall detection monitor 22 detects conditions of a fall, typically a state of zero gravity or reduced gravity, the precise threshold of which can be set by a qualified professional.

With the parameters such as timing, the threshold parameters of α and β adjustable, the qualified professional tunes the balance between false positives for a fall for an individual person, and false negatives. For example, if the person has a support network that the console 104 can call and the danger of injury is high in case of a fall, then the threshold to identify a fall can be set high (closer to 1 G, further from 0 G, more generally formulated as maximizing the size of the domain for satisfying condition B of FIG. 3) to risk false positives and send alerts or to proceed with the algorithm, for any event that remotely resembles a fall. In one setting, for example, this domain would include an accelerometer reading of 0.8 g. On the other hand, if all alerts are sent to 911 with no verification, especially if there is a significant social or financial cost for a false positive, and particularly if the user is judged not to be at risk of significant injury as a result of a fall, then the threshold to identify a fall can be set to risk false negatives and send alerts only for events that most rigorously fit the character of a fall. In one customized setting, for example, this domain would include an accelerometer reading of 0.1 G, or in the extreme, 0.0 G.

The user exhibits movement that the wearable fall detection monitor 22 determines to be characteristic of the wearer completing a fall, typically an impact, as represented by block 230. The accelerometer 40 associated with the wearable fall detection monitor 22 detects the motion, although an impact monitor can in certain cases also be used to detect impact. Again the details of the accelerometer 40 readings will depend on the nature of the fall. For a simple fall leading to a single-point contact with a surface, the acceleration 40 at that point of the body can be very high and the damage considerable, leading to shattering of even a healthy hip, and to shock waves transmitted through the body, where they are detected by an accelerometer 40. For a complex fall leading to multi-point contact with one or more surfaces, the fall is broken into multiple parts, each with lower acceleration upon impact. Again a qualified professional can set thresholds for determining that particular acceleration events are indicative of a fall of significance. These thresholds may depend on such factors as assessed bone fragility and weight.

Candidates for complex falls are the ones for which professionally settable parameters or thresholds for fall determination are particularly important. In one example, a user stumbles while climbing a stairs and catches himself with his hand or forearm against the stairs with no impact of the rest of the body against the stairs or walls. The accelerations and impacts are likely to be quite small, and the likelihood of significant injury quite small. It is a matter for professional judgment whether to set the device to consider such an event as a fall. In another example, the user stumbles while climbing a stairs and catches herself with her hand or forearm against the stairs with some degree of impact, possibly quite strong, of a part of her leg against the stairs or walls, jarring her body. Because of the location of the impact, the impact measured by sensors 30 may be quite small, and the acceleration no different than in the previous example. Yet it is possible that a particularly frail person may sustain significant leg injury and require help. It is a matter for professional judgment whether to set the device to consider such an event as a fall, and the degree to risk false positives. In yet a third example, a person partially misses a stair and falls on his ample buttocks and upper legs, sliding down the stairs. Thus, there was a zero G event at the beginning of the fall, but the impact was distributed over a considerable area of the body and stairs, and over several seconds of time. Even a seemingly very frail person has been known to suffer no injury from such a sequence of events. Again, it is a matter for professional judgment whether to set the device to consider such an event as a fall. The design of the present inventive device allows such a qualified person to make such settings to customize how the device identifies falls.

The user exhibits movement that the wearable fall detection monitor 22 determines to be characteristic of the last event in the sequence of the fall, that of the wearer not exhibiting significant signs of movement as represented by block 232. Again the details of the accelerometer 40 readings will depend on the nature of the motion. In case the person is motionless for a sufficiently long period of time, the fall detection system's 20 final logical condition changes to TRUE, meaning that the person is substantially not moving and is therefore likely to be unconscious or significantly injured, and the wearable fall detection monitor device 22 initiates a call for help. There are inherently two parameters characterizing this condition. One is the length of time that constitutes a "significant period of time." A qualified professional sets this parameter, or leaves it at the default value. The other parameter defines what constitutes "motionless" as represented by the distinction between condition D and condition E in FIG. 3. In case the accelerometer 40 indicates true zero motion, this is unambiguous. In case there is very slow motion the condition becomes ambiguous, although this ambiguity in motionlessness may be resolved in such cases through evaluation by a statistical classifier, by Shewhart control charts, or other similar means. A qualified professional can adjust this parameter for motionlessness as used by whatever algorithm that is used, or leaves it at the default value.

While this invention has been particularly shown and described with references to preferred embodiments thereof, it will be understood by those skilled in the art that various changes in form and details may be made therein without departing from the spirit and scope of the invention as defined by the appended claims.

For example, it is recognized that the device could be implanted under the skin of the user. Likewise, not all locations on the human body are equal with regard to the location of physiological sensors, and in many cases it may be desirable to embed sensors or other components of the system in clothing, shoes, protective gear, watches, prosthetics, etc.

For example, depending on the location the fall detection system 20 is used, the selection of the power system, the battery 138 could influence the arrangement. Battery size and weight are important human-factors consideration. It is expected that the battery weight will typically be approximately one half the weight of the wearable fall detection monitor 22. Battery size, weight, and run time are important ergonomic, reliability, and usability factors. Perhaps sometime in the future a device might run indefinitely on an arbitrarily small, light fuel cell that converts some compound of hydrogen very efficiently into electricity. At present the technical reality is that even in a well-optimized design, the sensor and analysis hardware consume a small, though significant amount of power. As a result, there is usually an important trade-off between battery size and run time for a given rate of power-consumption.

Radio usage places the single greatest demand for power. Thus if the radios are used more, the tradeoff is balanced in the direction of more power usage and therefore larger, heavier batteries. Therefore, minimizing radio usage is desirable, and it is important that the radio be shut down in standby mode when it is not specifically in use for communicating valuable information. Thus, it is desirable that the fall monitor is a dedicated device, or that any additional functionality, such as a time display to disguise the true purpose of wrist-worn device, be implemented with extraordinarily little power drain, with only a minimum of necessary information communicated, even to the extent of foregoing some of the storage and communication of detailed accelerometer data around the time of a candidate for a fall event. In a minimalist version, which might not be acceptable in light of the need to periodically verify continued proper function, there is communication only if there is an emergency, or very briefly at night to acknowledge that it is still present and functioning properly. In this way electrical power usage is minimized. Thus the tradeoff between battery weight and size versus battery longevity is biased in the desired direction.

How long "sufficient run time" is depends on the usage model of the wearable device. Use in an institutional setting, with active and ongoing device management and maintenance by caregivers, is a relatively undemanding usage model from the standpoint of run-time and battery management. A more demanding usage model is home use where frequent intervention for power management is typically not desirable or feasible.

In that the wearable fall monitor device 22 will not run indefinitely, the battery must be changed or recharged such as indicated above with charger 136 with respect to FIG. 7. For home use, the users of the device cannot always be relied on to change or recharge the battery. The users of the fall monitor are likely to be at least partially physically handicapped, and may suffer from perceptual and cognitive impairment as well. For example, a very high percentage of the elderly suffer from some degree of cognitive impairment, so that the same limitations that pose a problem for their remembering to push a manual call button or, if they do remember to try to push the button, then how to push the button, also pose a problem for their remembering to change a battery, or even how to change a battery if there is any recall required about the method to do so. Furthermore, even for users who are physically and cognitively capable of changing the battery, the requirement for routine maintenance could have a significant negative impact on usability and thereby decrease the availability of the device for its purpose.

Whether the battery is to be changed or recharged by the user or by someone else, or if the device is made available as a disposable that is simply replaced when the battery is exhausted, it is necessary to determine what a reasonable minimum run-time might be. One consideration is availability of personnel to perform maintenance functions. Because Medicare requires a monthly review of each patient or client by a superior of the everyday personnel who tend to the person, a medical doctor in the case of nurses from a Visiting Nurse Association (VNA) or a licensed nurse in the case of junior assistants, a one-month run-time might be considered an example absolute minimum for continuous operation for home-use as part of ongoing visiting care. Assuming that visiting caregivers will be able to replace or recharge the battery as needed, this configuration suggests that there would actually be multiple opportunities per month for a caregiver to do so. In reality the present embodiment is expected to support a battery life of 6 months to 2 years.

For home users who are not receiving ongoing home care or treatment under Medicare, the device should operate for periods considerably longer than a month without a battery change. Conventional stand-alone call-button wearable fall detection monitors generally operate for up to one year without battery change. Engineering analysis suggests that at this time a six to twenty-four-month period between battery changes is a reasonable engineering target for the wearable fall detection monitor 22. Although a six-month interval places more burden on the user or the caregiver than the one-year interval required for conventional radio call buttons, the additional functionality provided by the fall monitor more than compensates for the shorter battery life, and the users do not perceive a significant difference between a six month recharge cycle and a one year recharge cycle.

One model for battery management is a low-power, long-run embodiment in which the user, if adequately competent, or otherwise the caregiver or technician, replaces the fall monitor battery (or the entire device) on a periodic basis. Of presently commercially available battery technologies, a disposable lithium battery provides the highest power density in the smallest package. Hence, a lithium-chemistry battery charged by a trained technician is a desirable battery management option even if its expense makes the disposable option less attractive.

The present invention foresees arrangements in which more than one type of power source or power-management strategy is used. The problems outlined in this discussion—principally the problem of the need for long-term continuous device operation with no routine user maintenance are important and provide the framework within which alternative power and power management strategies can be analyzed. Those skilled in the art will recognize that all such alternative power management and provision strategies would fall within the spirit of the inventive device.

One of the advantages of the wearable fall detection monitor 22 as compared to the conventional call button device is that the wearable fall detection monitor 22 can monitor its battery charge (and other aspects of the device) and can inform caregivers (through the console communications system) and the user (through an LED or other external indicator) when the battery is running low. No such self-monitoring is provided by conventional radio call buttons, which are typically tested by calling users and asking them to push the call button. Thus the wearable fall detection monitor 22 user does not need to remember to change the battery or otherwise manage the device. The monitoring device can monitor its own state. Likewise, caregivers or the third-party monitoring service can remotely detect the failure of the wearable fall detection monitor 22 (due to missed verifications described above) or the console (due to missed call-ins during verifications described above) and can take action to remedy this situation.

What is claimed is:

1. A wearable device for a remote monitoring system, the wearable device positioned on a body of a user, the wearable device comprising:
    a data receiver to receive data transmitted from a single 3-D accelerometer positioned on the user;
    an analysis device to take the 3-D accelerometer data as input, the analysis device to analyze the 3-D accelerometer data during time intervals in real time using a parameterized algorithm with one or more stored parameters to determine if at least three distinct conditions that occur in a time order sequence associated with a fall have been met and to generate a report, wherein the parameters comprise acceleration thresholds, statistical thresholds from analysis of motion, and timing thresholds; and
    a transmitter to transmit the report to a remote location.

2. The wearable device for a remote monitoring system of claim 1, wherein the analysis device analyzes data in relation to a distinct condition, and the one or more stored parameters, each having a default value adjustable by qualified professionals to characterize the distinct condition for an individual user, or classes of users, the analysis device to use the parameterized algorithm to interpret the 3-D accelerometer data.

3. The wearable device for a remote monitoring system of claim 2, wherein the analysis device further provides an indicator of how closely the 3-D accelerometer data matches data characterizing a distinct condition.

4. The wearable device for a remote monitoring system of claim 3, wherein the analysis device uses reported values to indicate how closely the 3-D accelerometer data matches the parameters used by the algorithm.

5. The wearable device for a remote monitoring system of claim 1, further comprising a data diary for retaining the 3-D accelerometer data during time intervals to facilitate adjusting parameter settings for the user.

6. The wearable device for a remote monitoring system of claim 1, further comprising a data diary for retaining outputs from the algorithms.

7. The wearable device for a remote monitoring system of claim 1, wherein the wearable device further comprises a locator device.

8. The wearable device for a remote monitoring system of claim 1, wherein the wearable device further comprises an impact detector.

9. The wearable device for a remote monitoring system of claim 1, wherein the wearable device further comprises a second 3-D accelerometer.

10. A method for sensing whether a user has had a potentially disabling fall, comprising the steps of:
    providing a single 3-D accelerometer;
    providing a designated receiver;
    detecting whether a first acceleration during a first time interval is within a first specified range, thereby indicating that a first condition has been met;
    detecting whether a second acceleration during a second time interval is within a second specified range, thereby indicating that a second condition has been met and a fall is starting;
    detecting whether a third acceleration during a third time interval is within a third specified range, thereby indicating that a third condition has been met and an impact has occurred;
    waiting for a fourth time interval;
    detecting whether a fourth acceleration during a fifth time interval is within a fourth specified range, thereby indicating that a fourth condition has been met and the person is in need of assistance, wherein the detecting steps are conducted in real time using a parameterized algorithm with one or more stored parameters to indicate whether or not a condition has been met; and
    sending an alert to the designated receiver if the second, third, and fourth conditions are met, thereby indicating that a potentially disabling fall has occurred.

11. The method for sensing whether a user has had a potentially disabling fall of claim 10, further comprising the step of providing a second 3-D accelerometer.

12. The method for sensing whether a user has had a potentially disabling fall of claim 10, further comprising the step of providing an impact detector.

13. The method for sensing whether a user has had a potentially disabling fall of claim 10, wherein the method further comprises the step of detecting whether a fifth acceleration during the fifth time interval is within a fifth specified range, thereby indicating that a fifth condition has been met and the alert should not be sent.

14. The method for sensing whether a user has had a potentially disabling fall of claim 10, wherein the method further comprises the step of calculating the statistical sureness that a condition has been met.

15. The method for sensing whether a user has had a potentially disabling fall of claim 14, wherein the method further comprises the step of providing the data and statistical sureness to the designated receiver for use in modifying the specified ranges.

16. The method for sensing whether a user has had a potentially disabling fall of claim 14, wherein the method further comprises the step of providing the data and statistical sureness to the designated receiver for use in modifying the specified time intervals.

17. The method for sensing whether a user has had a potentially disabling fall of claim 14, further comprising the step of providing a locator device.

* * * * *